United States Patent
Honda

(10) Patent No.: US 11,589,912 B2
(45) Date of Patent: Feb. 28, 2023

(54) TREATMENT SYSTEM AND TREATMENT TOOL

(71) Applicant: Olympus Corporation, Hachioji (JP)

(72) Inventor: Yoshitaka Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 503 days.

(21) Appl. No.: 16/713,784

(22) Filed: Dec. 13, 2019

(65) Prior Publication Data

US 2020/0113616 A1 Apr. 16, 2020

Related U.S. Application Data

(63) Continuation of application No. PCT/JP2017/024346, filed on Jul. 3, 2017.

(51) Int. Cl.
*A61B 18/12* (2006.01)
*A61B 18/08* (2006.01)
(Continued)

(52) U.S. Cl.
CPC ............ *A61B 18/085* (2013.01); *A61B 18/12* (2013.01); *A61B 18/1445* (2013.01); *A61B 2018/00702* (2013.01)

(58) Field of Classification Search
CPC ... A61B 18/085; A61B 18/12; A61B 18/1445; A61B 2018/00172; A61B 2018/00642;
(Continued)

(56) References Cited

U.S. PATENT DOCUMENTS

| 6,666,875 B1 | 12/2003 | Sakurai et al. |
| 2007/0078452 A1 | 4/2007 | Sekino |

(Continued)

FOREIGN PATENT DOCUMENTS

| JP | 2000-271144 A | 10/2000 |
| JP | 2005-131285 A | 5/2005 |
| WO | 2010/109932 A1 | 9/2010 |

OTHER PUBLICATIONS

Jan. 7, 2020 International Preliminary Report on Patentability issued in International Patent Application No. PCT/JP2017/024346.

(Continued)

*Primary Examiner* — Daniel W Fowler
(74) *Attorney, Agent, or Firm* — Oliff PLC

(57) ABSTRACT

A treatment system comprises a power supply device and a treatment tool configured to communicate electrically with the power supply device so as to perform an operation on a treatment target. The treatment tool includes a sheath and an end effector configured to detachably attach to the sheath and being capable of bending with respect to the sheath. The end effector includes an electric element used to apply a treatment energy to the treatment target using an electric energy. The power supply device includes a processor. The processor sets to increase an output of the electric energy to be supplied to the electric element at in a second state. The sheath and the end effector are bent at a predetermined angle with respect to one another, compared with a first state where the sheath and the end effector are disposed straight in line with one another.

13 Claims, 12 Drawing Sheets

(51) Int. Cl.
*A61B 18/14* (2006.01)
*A61B 18/00* (2006.01)

(58) Field of Classification Search
CPC .. A61B 2018/00702; A61B 2018/00875; A61B 2018/1495
See application file for complete search history.

(56) References Cited

U.S. PATENT DOCUMENTS

| | | |
|---|---|---|
| 2011/0106141 A1 | 5/2011 | Nakamura |
| 2012/0101484 A1* | 4/2012 | Miersch ................ A61B 17/29 606/1 |
| 2014/0094795 A1* | 4/2014 | Keller ................. A61B 18/085 606/34 |
| 2015/0066022 A1 | 3/2015 | Shelton, IV et al. |
| 2015/0313667 A1* | 11/2015 | Allen, IV ........... A61B 18/1445 606/41 |

OTHER PUBLICATIONS

Sep. 26, 2017 International Search Report issued in International Patent Application No. PCT/JP2017/024346.

* cited by examiner

| β | β<βa (INCLUDING β1) | βa≦β<βb | βb≦β<βc | βc≦β (INCLUDING β2) |
|---|---|---|---|---|
| P | P1 | P2(>P1) | P3(>P2) | P4(>P3) |
| T | T1 | T2(>T1) | T3(>T2) | T4(>T3) |
| A | A1 | A2(>A1) | A3(>A2) | A4(>A3) |

| ρ | ρ<ρa (INCLUDING ρ2) | ρa≦ρ<ρb | ρb≦ρ<ρc | ρc≦ρ (INCLUDING ρ1) |
|---|---|---|---|---|
| P | P4(>P3) | P3(>P2) | P2(>P1) | P1 |
| T | T4(>T3) | T3(>T2) | T2(>T1) | T1 |
| A | A4(>A3) | A3(>A2) | A2(>A1) | A1 |

| α | α < αa (INCLUDING α2) | αa ≦ α < αb | αb ≦ α < αc | αc ≦ α (INCLUDING α1) |
|---|---|---|---|---|
| P | P4(>P3) | P3(>P2) | P2(>P1) | P1 |
| T | T4(>T3) | T3(>T2) | T2(>T1) | T1 |
| A | A4(>A3) | A3(>A2) | A2(>A1) | A1 |

TREATMENT SYSTEM AND TREATMENT TOOL

CROSS-REFERENCE TO RELATED APPLICATION

This application is a continuation application of PCT Application No. PCT/JP2017/024346 filed on Jul. 3, 2017, which is hereby incorporated by reference in its entirety.

TECHNICAL FIELD

The disclosed technology relates to a control apparatus for controlling the supply of an electric energy to a treatment tool that includes a pair of clamp members. The disclosed technology is also concerned with a treatment system including such a control apparatus, and a treatment tool for use with such a control apparatus.

DESCRIPTION OF THE RELATED ART

US Patent Application 2015/0066022A1 discloses a treatment tool that can grip a treatment target such as a biotissue or the like between a pair of clamp members of an end effector. With the treatment tool, the end effector can be bent or curved with respect to a sheath extending along a longitudinal axis thereof. With the treatment tool, when a drive shaft is moved in an axial direction thereof by a handle that is operated, the clamp members are closed relatively to each other, gripping the treatment target therebetween.

The amount of a gripping force acting between the clamp members varies between a state where the end effector is bent or curved and a neutral state where the end effector extends straight in line with the sheath. In addition, the amount of a gripping force acting between the clamp members varies according to a bend angle, or a curvature angle, of the end effector. In a treatment for applying a treatment energy to the treatment target gripped between the clamp members to seal, i.e., coagulate, or incise or otherwise process the treatment target, it is required that the treatment target be appropriately treated by the treatment energy even though the amount of the gripping force varies due to bending or curving of the end effector.

BRIEF SUMMARY OF EMBODIMENTS

The disclosed technology is directed to a treatment system comprises a power supply device and a treatment tool configured to communicate electrically with the power supply device so as to perform an operation on a treatment target. The treatment tool includes a sheath and an end effector configured to detachably attach to the sheath and being capable of bending with respect to the sheath. The end effector includes an electric element used to apply a treatment energy to the treatment target using an electric energy. The power supply device includes a processor. The processor sets to increase an output of the electric energy to be supplied to the electric element at in a second state. The sheath and the end effector are bent at a predetermined angle with respect to one another, compared with a first state where the sheath and the end effector are disposed straight in line with one another.

Another aspect of the disclosed technology is directed to a treatment system comprises a power supply device and a treatment tool configured to communicate electrically with the power supply device so as to perform an operation on a treatment target. The treatment tool comprises a tubular sheath having respective distal and proximal ends. A housing is detachably attach to the proximal end and an end effector is configured to detachably attach to the distal end and being capable of bending with respect to the tubular sheath. The end effector includes a pair of clamp members capable of being opened and closed with respect to one another. The pair of clamp members includes an electric element used to apply a treatment energy to the treatment target gripped between the clamp members using an electric energy. The power supply device includes a processor that acquires a parameter that varies according to a bent state of the end effector with respect to the tubular sheath and being related to an amount of a gripping force between the clamp members, and sets a control target value for controlling an output of the electric energy to the electric element based on the acquired parameter.

A further aspect of the disclosed technology is directed to a treatment tool comprises a housing. A tubular sheath having respective distal and proximal ends. The tubular sheath being detachably attached to the housing via the proximal end. An end effector is configured to detachably attach to the distal end and is capable of bending with respect to the tubular sheath. The end effector includes a pair of clamp members capable of being opened and closed with respect to one another. The pair of clamp members includes an electric element used to apply a treatment energy to the treatment target gripped between the clamp members using an electric energy. A sensor that outputs a detected result to cause a processor to acquire a parameter that varies according to a bent state of the end effector with respect to the tubular sheath and being related to an amount of a gripping force between the clamp members. The electric element is supplied with the electric energy that is output in a state where the processor performs output control at a control target value corresponding to the acquired parameter.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the disclosed technology to provide a control apparatus for applying an appropriate treatment energy to a treatment target gripped between clamp members, depending on the amount of a gripping force therebetween that is caused to vary by a bent state or a curved state of an end effector. It is also an object of the disclosed technology to provide a treatment system including such a control apparatus, and a treatment tool for use with such a control apparatus.

First Embodiment

A first embodiment of the disclosed technology will be described hereinafter with reference to FIGS. 1 through 23.

Figure 1:
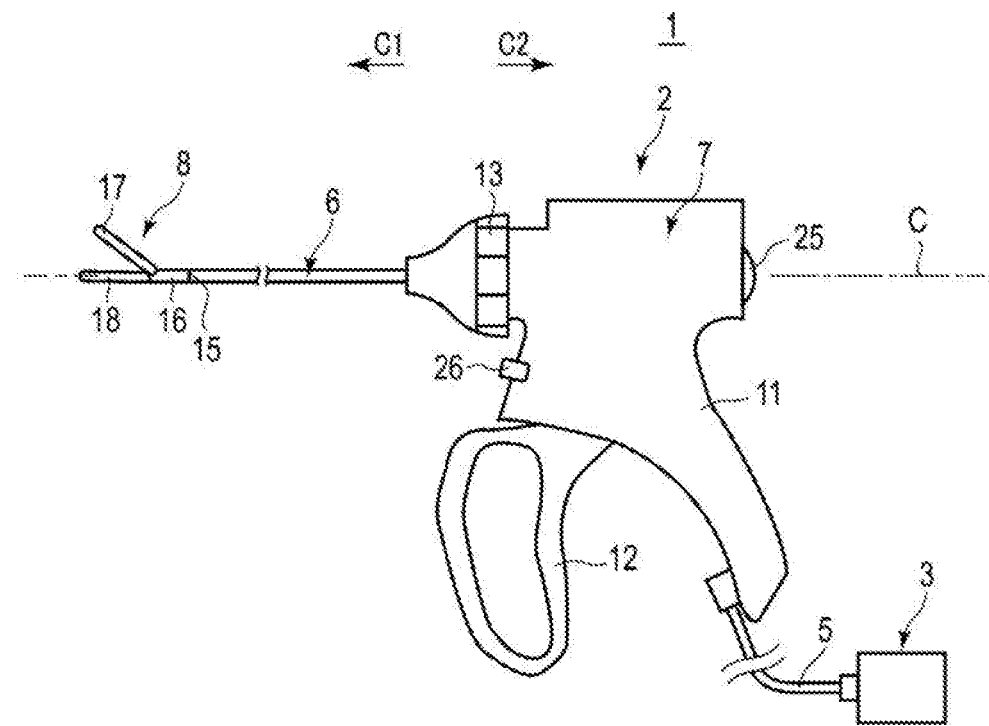
FIG. 1 is a schematic view illustrating a treatment system according to a first embodiment.

FIG. 1 is a view illustrating the makeup of a treatment system 1 according to the present embodiment. As illustrated in FIG. 1, the treatment system 1 includes a treatment tool 2 and a power supply device 3. The treatment tool 2 is detachably connected to the power supply device 3 by a cable 5. The treatment tool 2 includes a tubular sheath 6, a housing 7 that can be held, and an end effector 8. The sheath 6 has a longitudinal axis C that is straight or substantially straight as a central axis. One side pointed by a direction along the longitudinal axis C is referred to as a distal-end side, i.e., a side pointed by an arrow C1, whereas a side opposite the distal-end side is referred to as a proximal-end side, i.e., a side pointed by an arrow C2. The housing 7 is coupled to a proximal-end side of the sheath 6.

The housing 7 includes a grip 11 extending along directions transverse to the longitudinal axis C. A handle 12 is angularly movably attached to the housing 7. When the handle 12 is angularly moved with respect to the housing 7, the handle 12 is opened or closed with respect to the grip 11. According to the present embodiment, the cable 5 has an end connected to the grip 11 and another end detachably connected to the power supply device 3. According to the present embodiment, furthermore, a rotary knob 13 is mounted on the housing 7. When the rotary knob 13 is rotated with respect to the housing 7, the sheath 6 and the end effector 8 rotate in unison with the rotary knob 13 about the longitudinal axis C with respect to the housing 7. According to an example, the rotary knob 13 is dispensed with, and the sheath 6 and the end effector 8 are nonrotatable about the longitudinal axis C with respect to the housing 7.

Figure 2:
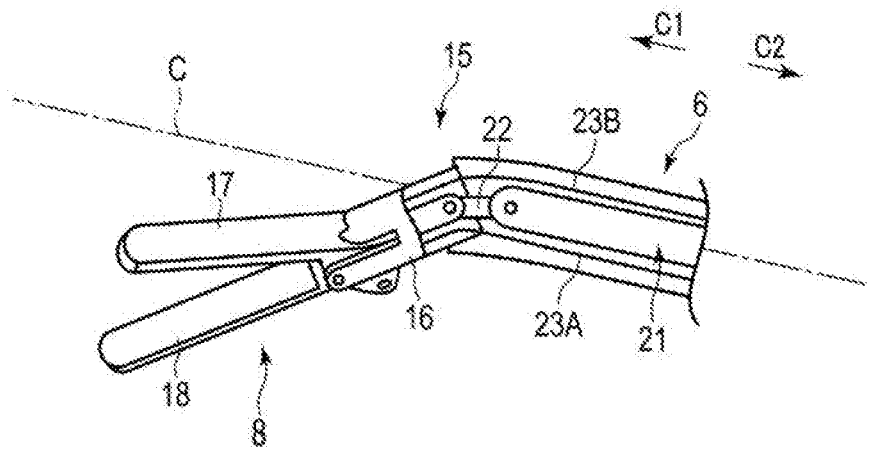
FIG. 2 is a schematic view illustrating an example of a structure of a distal-end portion of a sheath and an end effector according to the first embodiment.

FIG. 2 is a view illustrating an example of the structure of a distal-end portion of the sheath 6 and the end effector 8. According to the present embodiment, the end effector 8 is mounted on a distal-end portion of the sheath 6. The end effector 8 can be bent or curved with respect to the sheath 6, i.e., the longitudinal axis C. In the example illustrated in FIG. 2, a bending joint 15 is disposed between the sheath 6 and the end effector 8, and the end effector 8 is angularly movably mounted on the sheath 6 at the bending joint 15. When the end effector 8 is angularly moved with respect to the sheath 6, the end effector 8 is bent with respect to the sheath 6. According to an example, a curving tube, not depicted, instead of the bending joint 15, is disposed between the end effector 8 and the sheath 6. The curving tube includes a plurality of curving members, not depicted, each angularly movably coupled to adjacent curving members. When each of the curving members is angularly moved, the end effector 8 is curved with respect to the sheath 6.

The end effector 8 includes an effector body 16 and a pair of clamp members 17 and 18. The effector body 16 is mounted on the distal-end portion of the sheath 6 such that the effector body 16 can be bent or curved with respect to the sheath 6. The pair of clamp members 17 and 18 can be opened and closed with respect to each other. When the clamp members 17 and 18 are closed with respect to each other, the clamp members 17 and 18 can grip a treatment target such as a biotissue or the like therebetween.

According to an example, one of the clamp members 17 and 18 is integral with or fixed to the effector body 16, and the other is angularly movably mounted on the effector body 16. According to another example, both of the clamp members 17 and 18 are angularly movably mounted on the effector body 16. According to still another example, a rod member, not depicted, projects from a distal end of the effector body 16 toward the distal-end side, and the projecting portion of the rod member functions as one of the clamp members 17 and 18. The other of the clamp members 17 and 18 is angularly movably mounted on the effector body 16. According to this example, the rod member extends toward the distal-end side from a position that is spaced from a proximal end of the effector body 16, i.e., the bending joint 15, toward the distal-end side. If a portion of the rod member that passes between the end effector 8 and the sheath 6 is flexible, then the rod member may extend from within the housing 7 through the sheath 6 toward the distal-end side. In this case, the rod member has a distal-end portion that is bent or curved when the end effector 8 is bent or curved.

A drive shaft 21 has an end, i.e., a distal end, connected to the end effector 8. The drive shaft 21 extends along the longitudinal axis C within the sheath 6 or on an outer peripheral surface of the sheath 6, and is inserted into the housing 7 from a distal-end side thereof. The drive shaft 21 has another end portion, i.e., a proximal-end portion, coupled to the handle 12 within the housing 7. An operation to open or close the clamp members 17 and 18 with respect to each other is entered through the handle 12. When the handle 12 is operated to open or close the handle 12 with respect to the grip 11, the drive shaft 21 is moved along an axial direction of the drive shaft 21, i.e., the longitudinal axis C, with respect to the sheath 6. The clamp members 17 and 18 are thereby opened or closed with respect to each other. According to the present embodiment, consequently, the handle 12 and the drive shaft 21 function as members for transmitting a drive force to open or close the clamp members 17 and 18 with respect to each other to the end effector 8.

According to an example, the handle 12 is directly mounted on the drive shaft 21. According to another example, the handle 12 is mounted on the drive shaft 21 through another member such as a slider or the like. According to the example in which the rotary knob 13 is included, when the rotary knob 13 is rotated, the drive shaft 21 is rotated in unison with the sheath 6 and the end effector 8 about the longitudinal axis C.

A link mechanism 22 is disposed in a region of the drive shaft 21 which passes between the end effector 8 and the sheath 6, i.e., a region of the drive shaft 21 which passes through the bending joint 15 in the example illustrated in FIG. 2. The link mechanism 22 allows a region of the drive shaft 21 which is on the distal-end side with respect to the link mechanism 22 to be bent or curved when the end effector 8 is bent or curved with respect to the sheath 6, i.e., the longitudinal axis C. In other words, a distal-end portion of the drive shaft 21 is bent or curved when the end effector 8 is bent or curved. According to an example, a leaf spring or a rope, instead of the link mechanism 22, is disposed in the region of the drive shaft 21 which passes between the end effector 8 and the sheath 6.

A pair of elongate members 23A and 23B extend along the longitudinal axis C within the sheath 6. Each of the elongate members 23A and 23B is in the form of a wire, a leaf spring, or a bar. Alternatively, each of the elongate members 23A and 23B is in the form of a combination of some of these members. Each of the elongate members 23A and 23B has a distal end, i.e., one end, connected to the end effector 8. An operating member 25 such as an operating dial, an operating lever, or the like is mounted on the housing 7. The elongate members 23A and 23B are inserted into the housing 7 from the distal-end side thereof, and have proximal ends, i.e., other ends, coupled to the operating member 25 within the housing 7. An operation to move the elongate members 23A and 23B, i.e., an operation to bend or curve the end effector 8, is entered through the operating member 25. When the operating member 25 is operated to cause the elongate members 23A and 23B move along an axial direction, i.e., the longitudinal axis C, with respect to the sheath 6, the end effector 8 is bent or curved with respect to the sheath 6. According to the present embodiment, therefore, the operating member 25 and the elongate members 23A and 23B function as members for transmitting a drive force to bend or curve the end effector 8 with respect to the sheath 6.

According to an example, the operating member 25 is directly mounted on the elongate members 23A and 23B, and transmits a drive force directly to the elongate members 23A and 23B. According to another example, the operating member 25 is mounted on the elongate members 23A and 23B through another member such as a gear or the like, and transmits a drive force through the other member to the elongate members 23A and 23B. According to the example in which the rotary knob 13 is included, when the rotary knob 13 is rotated, the elongate members 23A and 23B are rotated in unison with the sheath 6, the end effector 8, and the drive shaft 21 about the longitudinal axis C. At this time, however, the operating member 25 and the member that transmits a drive force from the operating member 25 to the elongate members 23A and 23B may be rotated in unison with the drive shaft 21 and the end effector 8 about the longitudinal axis C or may not be rotated in unison with the drive shaft 21, etc. Each of the elongate members 23A and 23B is flexible, and has a distal-end portion that can be bent or curved when the end effector 8 is bent or curved.

According to the present embodiment, an operating button 26 is mounted as an operating member on the housing 7. An operation to supply an electric energy from the power supply device 3 to the treatment tool 2 is entered through the operating button 26. According to an example, instead of or in addition to the operating button 26, a foot switch or the like that is separate from the treatment tool 2 is included as an operating member through which to enter an operation to supply an electric energy from the power supply device 3 to the treatment tool 2.

Figure 3:
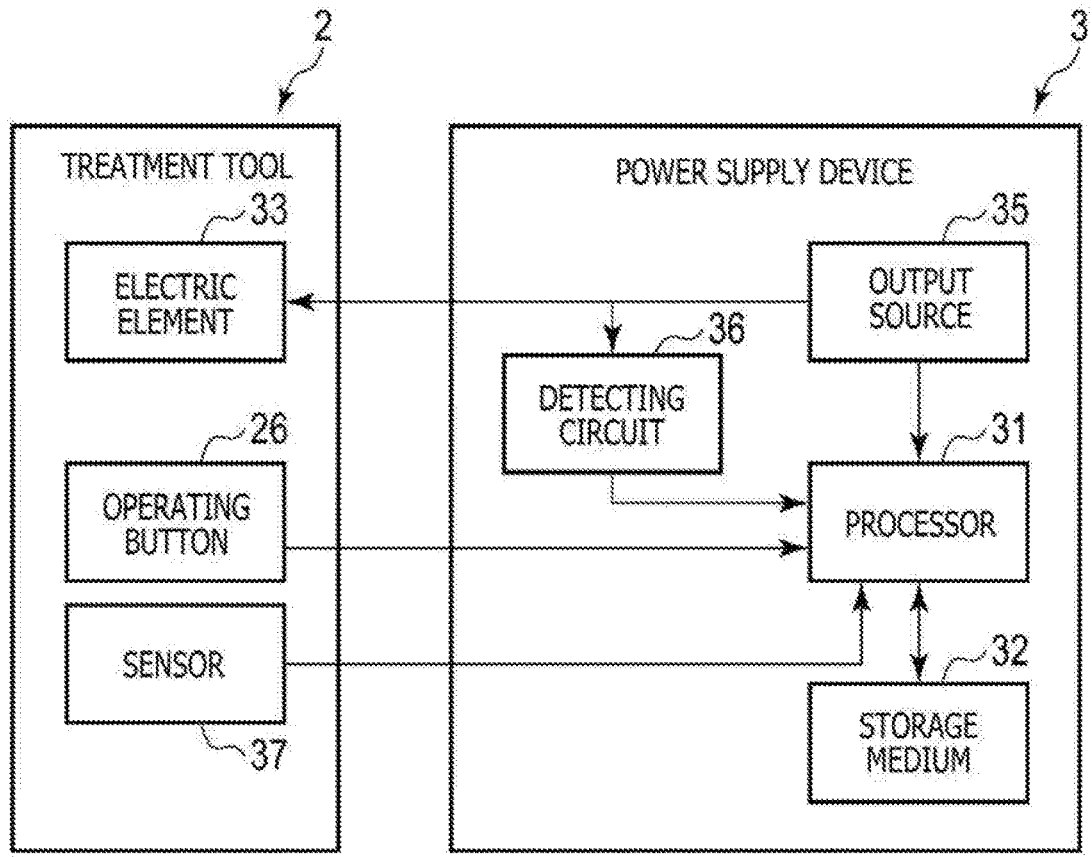
FIG. 3 is a block diagram schematically illustrating an arrangement for controlling an electric energy to a treatment tool according to the first embodiment.

FIG. 3 is a diagram illustrating an arrangement for controlling the supply of an electric energy to the treatment tool 2. As illustrated in FIG. 3, the power supply device 3 includes a processor or controller 31 and a storage medium 32. The processor 31 is in the form of an integrated circuit, a circuit arrangement, or a circuitry, or the like, including a CPU (Central Processing Unit), an ASIC (Application Specific Integrated Circuit), an FPGA (Field Programmable Gate Array), or the like. The power supply device 3 may include only one processor 31 or a plurality of processors 31. According to the present embodiment, the processor 31 functions as a control apparatus for controlling the treatment system 1 in its entirety. The processor 31 performs processing sequences according to programs stored in the processor 31 or the storage medium 32. The storage medium 32 stores processing programs used by the processor 31 and parameters, functions, tables, etc. used in arithmetic operations of the processor 31.

The processor 31 determines whether or not an operation is entered through the operating button 26, i.e., whether an operation input through the operating button 26 is ON or OFF. According to an example, a switch, not depicted, is disposed in the housing 7 in association with the operating button 26, and switches between ON and OFF according to an operation on the operating button 26. The processor 31 determines whether or not an operation is entered through the operating button 26 based on whether the switch is ON or OFF.

The treatment tool 2 includes an electric element 33 that is supplied with the electric energy from the power supply device 3. The power supply device 3 includes an output source 35 capable of outputting the electric energy to be supplied to the electric element 33. The output source 35 includes a converting circuit, a transformer, etc., and functions as a drive circuit. The output source 35 converts electric power from a battery power supply, an outlet power supply, or the like into the electric energy to be supplied to the electric element 33. The output source 35 then outputs the converted electric energy. The electric energy output from the output source 35 is supplied to the electric element 33 through an electric path or the like that extends through the cable 5 and the housing 7. When the electric element 33 is energized by being supplied with the electric energy, it can apply a treatment energy to the treatment target gripped between the clamp members 17 and 18. While an operation is being entered through the operating button 26, the processor 31 controls the output of the electric energy from the output source 35 to the electric element 33. The state where the treatment energy is applied to the treatment target on the end effector 8 is thus controlled.

According to an example, an electrode is included as the electric element 33 in each of the clamp members 17 and 18. The output source 35 supplies each of the electrodes with high-frequency electric power as electric energy. The electrodes that are supplied with high-frequency electric power have potentials that are different from each other. Consequently, when high-frequency electric power is supplied to each of the electrodes while the treatment target is being gripped between the clamp members 17 and 18, a high-frequency electric current flows through the treatment target between the electrodes, and is applied as a treatment energy to the treatment target.

According to another example, a heater is included as the electric element 33 in the end effector 8. The output source 35 supplies DC (Direct Current) electric power or AC (Alternating Current) electric power as electric energy to the heater. When the heater is supplied with electric energy, the heater generates heater heat, and the generated heater heat is transmitted through the end effector 8. Consequently, when the heater is supplied with electric energy while the treatment target is being gripped between the clamp members 17 and 18, heater heat is applied as a treatment energy to the treatment target.

According to an example, a plurality of ultrasonic transmitting elements are included as the electric element 33 in the end effector 8 or the like. When electric energy is supplied to each of the plurality of ultrasonic transmitting elements, each of the ultrasonic transmitting elements transmits ultrasound. The ultrasound transmitted from each of the ultrasonic transmitting elements is focused to produce HIFU (High Intensity Focused Ultrasound). According to the present example, the HIFU is applied as a treatment energy to the treatment target.

According to another example, an ultrasonic transducer is included as the electric element 33 in the effector body 16 or the housing 7. In this case, one of the clamp members 17 and 18 is in the form of the rod member, not depicted, referred to hereinbefore, that projects from the distal end of the effector body 16 toward the distal-end side. The ultrasonic transducer is connected to the rod member on the proximal-end side thereof. According to the present example, AC electric power having a frequency in a predetermined frequency range is supplied as electric energy from the output source 35 to the ultrasonic transducer. When electric energy is supplied to the ultrasonic transducer, the ultrasonic transducer produces ultrasonic vibrations that are transmitted through the rod member to one of the clamp members 17 and 18. Consequently, when electric energy is supplied to the ultrasonic transducer while the treatment target is being gripped between the clamp members 17 and 18, ultrasonic vibrations are applied as a treatment energy from one of the clamp members 17 and 18 to the treatment target.

According to an example, a plurality of elements including the electrodes, the heater, the ultrasonic transmitting elements, and the ultrasonic transducer referred to hereinbefore are included as electric elements. In this case, output sources 35 are included in association with the respective electric elements 33 and are capable of simultaneously applying a plurality of kinds of treatment energies to the treatment target. The processor 31 controls the output of the electric energy from the output sources 35 to the corresponding electric elements 33.

According to the present embodiment, the power supply device 3 includes a detecting circuit 36. The detecting circuit 36 detects an output electric current I and an output electric voltage V from the output source 35. The detecting circuit 36 transmits detected results of the output electric current I and the output electric voltage V to the processor 31. The processor 31 now acquires information regarding the output electric current I and information regarding the output electric voltage V. Based on the output electric current I and the output electric voltage V that have been acquired, the processor 31 calculates an output electric power P from the output source 35, an impedance of a circuit through which the output electric current I flows, and the like. According to the example in which the heater is included as the electric element 33, for example, the processor 31 calculates a resistance of the heater based on the output electric current I and the output electric voltage V. Based on the calculated resistance and the relationship between resistances of the heater and temperatures of the heater that are stored in the storage medium 32 or the like, the processor 31 calculates a temperature of the heater. Furthermore, according to the example in which the ultrasonic transducer is included as the electric element 33, for example, the processor 31 calculates an amplitude of the produced ultrasonic vibrations based on the output electric current I. The amplitude of the produced ultrasonic vibrations varies with the output electric current I such that the larger the output electric current I is, the larger the amplitude is. The processor 31 controls the output of the electric energy to the electric element 33 based on the output electric current I and the output electric voltage V that have been acquired and the output electric power P, the impedance, and the like that have been calculated.

According to the example in which there are a plurality of electric elements and a plurality of output sources 35, detecting circuits 36 are included in association with the respective output sources 35. Output electric currents (I) and output electric voltages (V) from the output sources 35 respectively to the corresponding electric elements 33 are detected by the corresponding detecting circuits 36.

According to the present embodiment, the treatment tool 2 includes a sensor 37. The sensor 37 outputs a detected result about a detection target, and the output detected result is transmitted to the processor 31. Based on the detected result from the sensor 37, the processor 31 acquires a parameter that varies according to a bent state or a curved state of the end effector 8 with respect to the sheath 6 and that is related to the amount of a gripping force between the clamp members 17 and 18. Based on the acquired parameter, the processor 31 controls the output of the electric energy from the output source 35 to the electric element 33. At this time, the processor 31 sets a control target value based on the parameter for the control of the output of the electric energy to the electric element 33. According to an example, a function or table that represents the relationship between parameters and control target values is stored in the storage medium 32 or the like. In this case, the processor 31 acquires the function or table that represents the relationship between parameters and control target values from the storage medium 32 or the like. Then, the processor 31 sets a control target value based on the acquired parameter and the relationship described hereinbefore that is represented by the function or table.

For treating a treatment target using the treatment system 1, the surgeon holds the housing 7 and inserts the end effector 8 into a body cavity such as an abdominal cavity or the like. Then, the surgeon adjusts the angular position of the end effector 8 about the longitudinal axis C with the rotary knob 13 and adjusts the bent state or the curved state of the end effector 8 with respect to the sheath 6 with the operating member 25, thereby adjusting the position and posture of the end effector 8 and placing the treatment target between the clamp members 17 and 18. Then, while the treatment target is being placed between the clamp members 17 and 18, the surgeon closes the handle 12 with respect to the grip 11 thereby to close the clamp members 17 and 18 toward each other to grip the treatment target between the clamp members 17 and 18. With the treatment target being thus gripped, the surgeon enters an operation input with the operating button 26. The processor 31 now outputs electric energy to the electric element 33 of the treatment tool 2, thus applying a treatment energy to the gripped treatment target.

Figure 4:
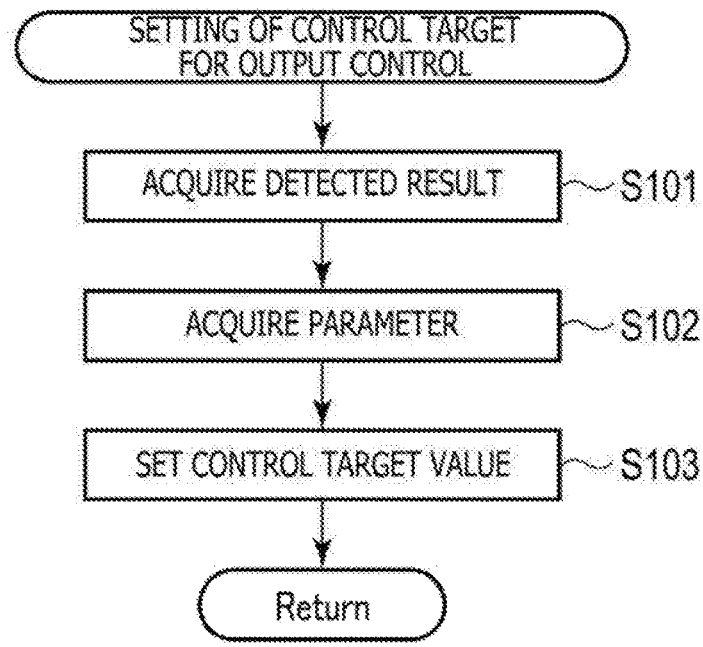
FIG. 4 is a flowchart illustrating a processing sequence, carried out by a processor according to the first embodiment, for setting a control target for the control of an output of an electric energy supplied to an electric element.

FIG. 4 illustrates a processing sequence carried out by the processor 31 for setting a control target for the control of the output of the electric energy to the electric element 33. The processing sequence illustrated in FIG. 4 is carried out prior to the output of the electric energy to the electric element 33. As illustrated in FIG. 4, for setting a control target for the output control, the processor 31 acquires a detected result from the sensor 37 in Step S101. Then, based on the detected result from the sensor 37, the processor 31 acquires a parameter that varies according to a bent state or a curved state of the end effector 8 with respect to the sheath 6 and that is related to the amount of a gripping force between the clamp members 17 and 18 in Step S102. At this time, the processor 31 acquires a detection target for the sensor 37 as a parameter or calculates a parameter based on the detected result from the sensor 37. Then, the processor 31 sets a control target value for the output control based on the acquired parameter in Step S103. At this time, the processor 31 sets a control target value based on the function or table, stored in the storage medium 32 or the like, that represents the relationship between parameters and control target values, and the acquired parameters.

According to an example, in the control of the output of the electric energy to the electric element 33, the processor 31 is able to perform at least either one of a constant electric current control process for making the electric current value of the output electric current I chronologically constant or substantially constant, a constant electric voltage control process for making the electric voltage value of the output electric voltage V chronologically constant or substantially constant, and a constant electric power control process for making the output electric power P chronologically constant or substantially constant. For example, in the case where the processor 31 is able to perform the constant electric current control process, the processor 31 sets the electric current value in the constant electric current control process as a control target value based on the parameter referred to hereinbefore. Similarly, in the case where the processor 31 is able to perform the constant electric voltage control process, the processor 31 sets the electric voltage value in the constant electric voltage control process as a control target value based on the parameter referred to hereinbefore. In the case where the processor 31 is able to perform the constant electric power control process, the processor 31 sets the output electric power P in the constant electric power control process as a control target value based on the parameter referred to hereinbefore.

According to an example, in the control of the output of the electric energy to the electric element 33, the processor 31 is able to perform a control process for increasing at least either one of the output electric current I, the output electric voltage V, and the output electric power P at a chronologically constant rate of increase. In this case, the processor 31 sets the chronological rate of increase for either one of the output electric current I, the output electric voltage V, and the output electric power P as a control target value. According to an example, a heater is included as the electric element 33, and the processor 31 is able to perform a temperature control process for having the heater reach a target temperature T and maintaining the heater at the target temperature T. In this case, the processor 31 sets the target temperature T in the temperature control process as a target control value based on the parameter referred to hereinbefore. According to another example, an ultrasonic transducer is included as the electric element 33, and the processor 31 performs a control process for keeping the amplitude of ultrasonic vibrations chronologically constant or substantially constant at a target amplitude A. In this case, the processor 31 sets the target amplitude A in the vibration control process as a target control value based on the parameter referred to hereinbefore. While the amplitude of ultrasonic vibrations is being kept chronologically constant or substantially constant at the target amplitude A, the electric current value of the output electric current I is kept chronologically constant or substantially constant at a magnitude corresponding to the target amplitude A.

Examples of the sensor 37, examples of the parameter acquired by the processor 31, and examples of the function or table that represents the relationship between parameters and control target values will hereinafter be described.

First Example

Figure 5:
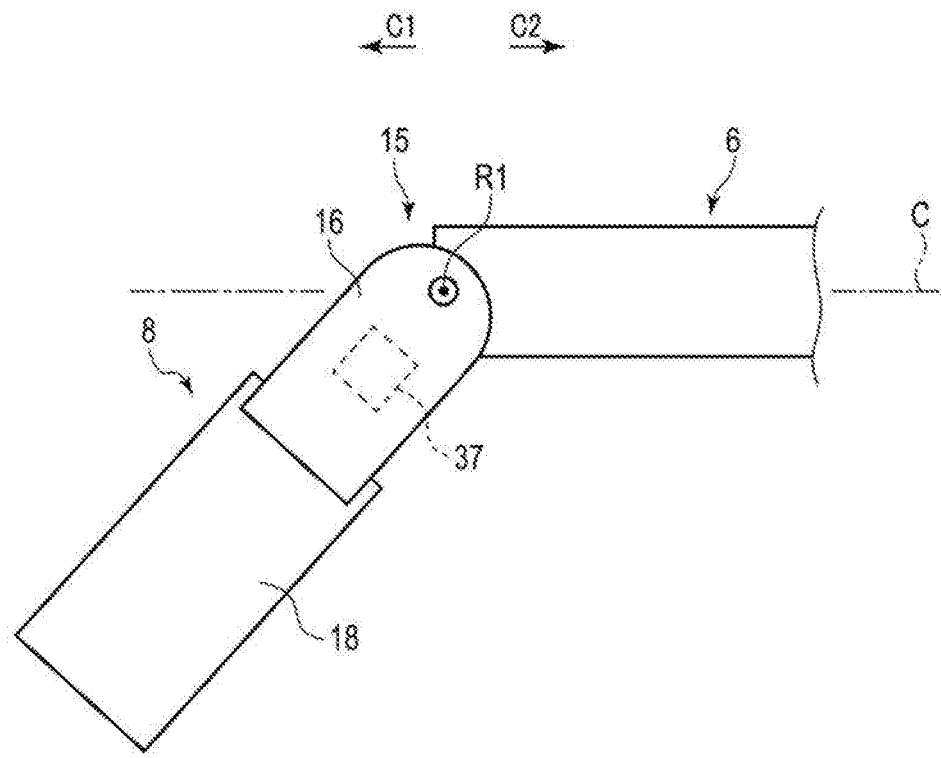
FIG. 5 is a schematic view illustrating a sensor according to a first example.

According to a first example illustrated in FIG. 5, an angle sensor is mounted as the sensor 37 on the end effector 8, for example. The angle sensor may be a known sensor such as a gyrosensor, a Hall effect sensor, a rotary encoder, an optical encoder, a potentiometer, or the like, for example. According to the present example, the end effector 8 is bent with respect to the sheath 6 when it turns about a turn axis R1. The sensor 37 detects the angular position of the end effector 8 about the turn axis R1 with respect to the sheath 6. According to the present example, the storage medium 32, for example, stores information regarding the angular position of the end effector 8 in the neutral state where the end effector 8 extends straight in line with the sheath 6. The processor 31 calculates and acquires a bend angle $\beta$ of the end effector 8 as a parameter based on the detected result from the sensor 37. The bend angle $\beta$ of the end effector 8 acquired by the processor 31 represents a parameter that varies according to the bent state of the end effector 8. In the neutral state where the end effector 8 extends straight in line with the sheath 6, i.e., the longitudinal axis C, the bend angle $\beta$ is 0°.

According to an example, the curving tube referred to hereinbefore that includes the plurality of curving members is included, and the sensor 37 as the angle sensor detects angular positions of the curving members about respective rotational axes or rotational centers as a detection target. According to the present example, the storage medium 32, for example, stores information regarding the angular positions of the curving members in the neutral state. The processor 31 calculates and acquires a curvature angle of the end effector 8 as a parameter based on the detected result from the sensor 37. The curvature angle of the end effector 8 acquired by the processor 31 represents a parameter that varies according to the curved state of the end effector 8.

The amount F of a gripping force between the clamp members 17 and 18 varies according to an axial force acting from the drive shaft 21 on the end effector 8 such that the larger the axial force transmitted from the drive shaft 21 to the end effector 8 is, the larger the amount F of the gripping force is. As described hereinbefore, when the end effector 8 is bent or curved with respect to the sheath 6, the distal-end portion of the drive shaft 21 is bent or curved. In the case where the distal-end portion of the drive shaft 21 is bent or curved, the axial force transmitted by the drive shaft 21 is resolved or suffers a loss due to friction or the like in the link mechanism 22 or the like. Then, the axial force that has been resolved or suffered a loss is transmitted from the drive shaft 21 to the end effector 8. Therefore, providing other conditions such as the kind of the treatment target, the amount of an operating force on the handle 12, etc. remain the same, the axial force transmitted from the drive shaft 21 to the end effector 8 is lowered in the state where the distal-end portion of the drive shaft 21 is bent or curved, compared with the neutral state where the drive shaft 21 is straight in its entirety. Providing the other conditions remain the same, the larger the bend angle, or the curvature angle, is, the larger the reduction in the axial force due to the resolving of the same, etc., and hence the smaller the axial force transmitted to the end effector 8 is.

Figure 6:
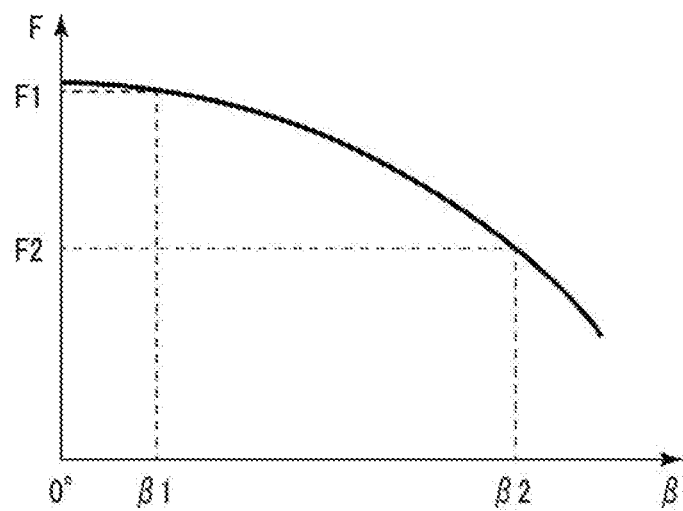
FIG. 6 is a schematic diagram illustrating by way of example the relationship between bend angles of an end effector and amounts of a gripping force between clamp members.

FIG. 6 illustrates by way of example the relationship between bend angles $\beta$ of the end effector 8 and amounts F of a gripping force between the clamp members 17 and 18. In FIG. 6, the horizontal axis represents the bend angles $\beta$ and the vertical axis the amounts F of the gripping force. As described hereinbefore, when the end effector 8 is bent or curved, the axial force transmitted to the end effector 8 is lowered compared with the neutral state where the bend angle, or the curvature angle, $\beta$ of the end effector 8 is 0°. Therefore, as illustrated in FIG. 6, in the state where the end effector 8 is bent or curved, providing the other conditions remain the same, the amount F of the gripping force between the clamp members 17 and 18 is lowered compared with the neutral state. Furthermore, providing the other conditions remain the same, the larger the bend angle, or the curvature angle, $\beta$ is, the smaller the axial force transmitted to the end effector 8 is and hence the smaller the amount F of the gripping force between the clamp members 17 and 18 is. Consequently, the bend angle, or the curvature angle, $\beta$ of the end effector 8 that is acquired by the processor 31 acts as a parameter that affects the amount F of the gripping force between the clamp members 17 and 18 and that is related to the amount F of the gripping force.

In the case where the relationship illustrated in FIG. 6, for example, is established, in a state where the bend angle $\beta$ is a first angle $\beta 1$, the processor 31 acquires a first value ($\beta 1$) as a parameter, and the amount F of the gripping force between the clamp members 17 and 18 becomes a first amount F1 of force. In a state where the bend angle $\beta$ is a second angle $\beta 2$ that is larger than the first angle $\beta 1$, the processor 31 acquires a second value ($\beta 2$) that is larger than the first value ($\beta 1$) as a parameter, and the amount F of the gripping force between the clamp members 17 and 18 becomes a second amount F2 of force.

According to the present example, after the bend angle, or the curvature angle, $\beta$ of the end effector 8 is adjusted and before electric energy starts to be output to the electric element 33, the processor 31 performs the processing sequence illustrated in FIG. 4, thereby setting a control target value. According to the present example, furthermore, a table illustrated in FIG. 7 that illustrates the relationship between bend angles $\beta$ as a parameter and control target values, for example, is used in setting a control target value. In the case where a control target value is to be set using the table illustrated in FIG. 7, either one of the output electric power P in the constant electric power control process described hereinbefore, the target temperature T in the temperature control process described hereinbefore, and the target amplitude A in the vibration control process described hereinbefore is set as a control target value.

Figures 7, 8:
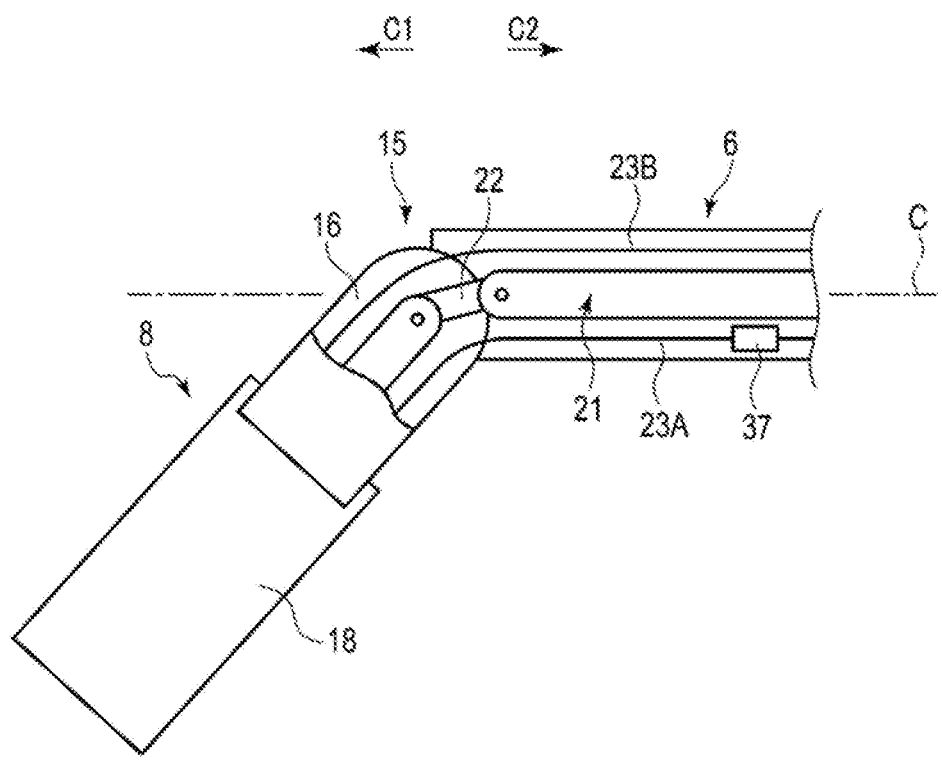
FIG. 7 is a schematic diagram illustrating by way of example a table used in setting a control target value based on a parameter, i.e., a bend angle.
FIG. 8 is a schematic view illustrating a sensor according to a second example.

According to the relationship represented by the table illustrated in FIG. 7, the output electric power P, the target temperature T, and/or the target amplitude A set as a control target value increases stepwise at each of threshold values $\beta a$, $\beta b$, and $\beta c$ according to an increase in the bend angle $\beta$ acquired as a parameter. In the constant electric power control process described hereinbefore, the larger the output electric power P is, the higher the output of the electric energy to the electric element 33 is. In the temperature control process described hereinbefore, the higher the target temperature T is, the higher the output of the electric energy to the electric element 33 is. In the vibration control process described hereinbefore, the larger the target amplitude A is, the higher the output of the electric energy to the electric element 33 is. According to the relationship represented by the table illustrated in FIG. 7, therefore, the output of the electric energy to the electric element 33 increases stepwise at each of the threshold values $\beta a$, $\beta b$, and $\beta c$ according to an increase in the bend angle $\beta$.

For example, in the case where the treatment target is gripped in the state where the bend angle, or the curvature angle, $\beta$ is the first angle $\beta 1$, the processor 31 acquires the first value $\beta 1$ that is smaller than the threshold value $\beta a$ as a parameter, and the amount F of the gripping force between the clamp members 17 and 18 becomes the first amount F1 of force. In this case, the processor 31 sets the output electric power P as a control target value to an electric power P1 and/or sets the target temperature T as a control target value to a temperature T1 based on the table illustrated in FIG. 7. At this time, instead of or in addition to the setting described hereinbefore, the processor 31 may set the target amplitude A as a control target value to an amplitude A1. Moreover, in the case where the treatment target is gripped in the state where the bend angle, or the curvature angle, β is of the second angle β2 that is larger than the first angle β1, the processor 31 acquires the second value β2 that is equal to or larger than the threshold value βc as a parameter, and the amount F of the gripping force between the clamp members 17 and 18 becomes the second amount F2 of force that is smaller than the first amount F1 of force. In this case, the processor 31 sets the output electric power P as a control target value to an electric power P4 that is larger than the electric power P1 and/or sets the target temperature T as a control target value to a temperature T4 that is higher than the temperature T1 based on the table illustrated in FIG. 7. At this time, instead of or in addition to the setting described hereinbefore, the processor 31 may set the target amplitude A as a control target value to an amplitude A4 that is larger than the amplitude A1.

Since the control target value is set as described hereinbefore, according to the present example, in the state where the bend angle β is large, such as the state where the bend angle β is of the second angle β2 or the like, the control target value that is set is large and the output of the electric energy to the electric element 33 increases compared with the state where the bend angle β is small or 0°, such as the state where the bend angle β is the first angle β1 or the like. Furthermore, since the control target value is set as described hereinbefore, according to the present example, in the state where the amount F of the gripping force is small, such as the state where the amount F of the gripping force is the second amount F2 of force or the like, the control target value that is set is large and the output of the electric energy to the electric element 33 increases compared with the state where the amount F of the gripping force is large, such as the state where the amount F of the gripping force is the first amount F1 of force or the like.

According to the present example, as described hereinbefore, the control target value in the control of the output to the electric element 33 is adjusted depending on the amount F of the gripping force that varies due to bending or curving of the end effector 8. In a state where the amount F of the gripping force is lowered due to bending or curving of the end effector 8, the output to the electric element 33 is set to a higher level. Therefore, even in the state where the amount F of the gripping force is lowered due to bending or curving of the end effector 8, the effect of the reduction in the amount F of the gripping force on the treatment is canceled out by the effect of the increase in the output of the electric energy on the treatment. Consequently, even when the amount F of the gripping force is varied due to bending or curving of the end effector 8, the output of the electric energy is adjusted depending on the amount F of the gripping force, allowing the treatment target to be appropriately treated by the treatment energy.

Also in the case where the electric current value of the output electric current I in the constant electric current control process described hereinbefore is set as a control target value, in the case where the electric voltage value of the output electric voltage V in the constant electric voltage control process described hereinbefore is set as a control target value, and in the case where the rate of increase of either one of the output electric current I, the output electric voltage V, and the output electric power P is set as a control target value, the control target values are set using a table, a function, or the like similar to the table illustrated in FIG. 7. Therefore, even according to the example in which an electric current value and/or an electric voltage value is set as a control target value, in the state where the bend angle β is large, the control target value that is set is large and the output of the electric energy to the electric element 33 increases compared with the state where the bend angle β is small or 0°. Furthermore, in the state where the amount F of the gripping force is small, the control target value that is set is large and the output of the electric energy to the electric element 33 increases compared with the state where the amount F of the gripping force is large. In examples to be described hereinafter, etc., a case in which the output electric power P in the constant electric power control process, the target temperature T in the temperature control process, and/or the target amplitude A in the vibration control process is set as a control target value will be described. However, the invention is similarly applicable to cases in which other control target values are set.

Second Example

According to a second example illustrated in FIG. 8, a positional sensor is mounted as the sensor 37 on the elongate member 23A. The positional sensor may be a known sensor such as an optical sensor, a magnetic sensor, or the like, for example. According to the present example, the sensor 37 detects the position of the elongate member 23A with respect to the sheath 6, as a detection target. According to the present example, the storage medium 32, for example, stores information regarding the position of the elongate member 23A in the neutral state where the end effector 8 extends straight in line with the sheath 6. The processor 31 calculates and acquires a displacement c of the elongate member 23A from the neutral state as a parameter based on the detected result from the sensor 37. As described hereinbefore, the elongate member 23A is a member for transmitting a drive force to bend or curve the end effector 8. The end effector 8 is bent or curved when the elongate member 23A is moved along an axial direction thereof. Therefore, the displacement c of the elongate member 23A that is acquired by the processor 31 acts as a parameter that varies according to a bent state or a curved state of the end effector 8.

Figure 9:
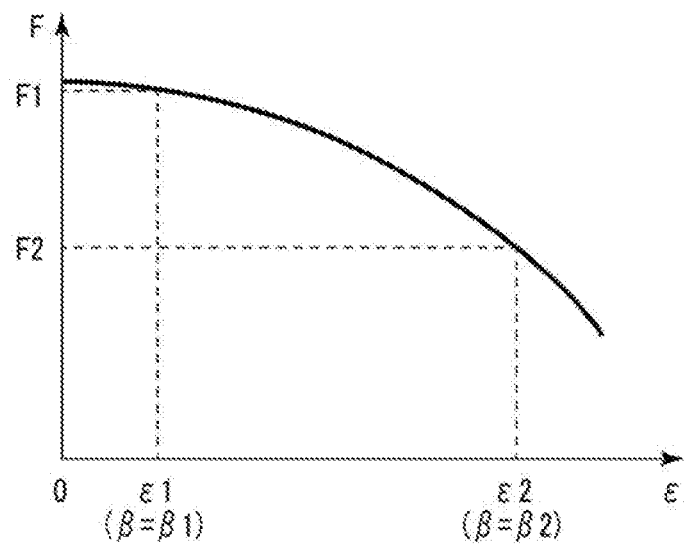
FIG. 9 is a schematic diagram illustrating by way of example the relationship between displacements of an elongate member and amounts of a gripping force between clamp members.

FIG. 9 illustrates by way of example the relationship between displacements c of the elongate member 23A and amounts F of a gripping force between the clamp members 17 and 18. In FIG. 9, the horizontal axis represents the displacements c and the vertical axis the amounts F of the gripping force. As described hereinbefore, when the end effector 8 is bent or curved, providing the other conditions remain the same, the amount F of the gripping force between the clamp members 17 and 18 is lowered compared with the neutral state. Providing the other conditions remain the same, the larger the bend angle, or the curvature angle, β is, the smaller the amount F of the gripping force between the clamp members 17 and 18 is. Since the displacement c of the elongate member 23A that is acquired by the processor 31 varies according to the bend angle, or the curvature angle, β of the end effector 8, the displacement c acts as a parameter that affects the amount F of the gripping force between the clamp members 17 and 18 and that is related to the amount F of the gripping force. As illustrated in FIG. 9, providing the other conditions remain the same, the larger the displacement, i.e., the absolute value of the displacement, c of the elongate member 23A from the neutral position is, the smaller the amount F of the gripping force is.

In the case where the relationship illustrated in FIG. 9, for example, is established, when the elongate member 23A is displaced a first displacement ε1 from the neutral state, the bend angle β becomes the first angle β1, and the processor 31 acquires a first value (ε1) as a parameter. At this time, the amount F of the gripping force between the clamp members 17 and 18 becomes a first amount F1 of force. When the elongate member 23A is displaced a second displacement ε2 that is larger than the first displacement ε1 from the neutral state, the bend angle β becomes the second angle β2 that is larger than the first angle β1, and the processor 31 acquires a second value (ε2) that is larger than the first value (ε1) as a parameter. At this time, the amount F of the gripping force between the clamp members 17 and 18 becomes a second amount F2 of force that is smaller than the first amount F1 of force.

Figure 10:
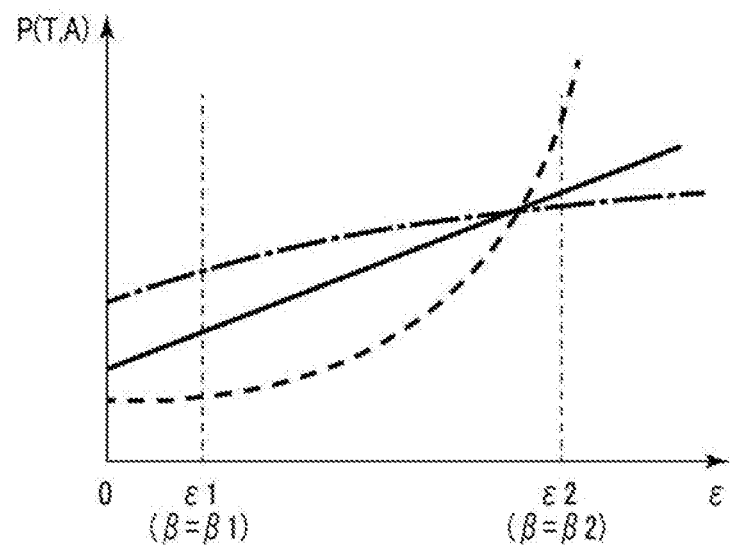
FIG. 10 is a schematic diagram illustrating by way of example functions used in setting a control target value based on a parameter, i.e., a displacement of the elongate member.

According to the present example, too, after the bend angle, or the curvature angle, β of the end effector 8 is adjusted and before electric energy starts to be output to the electric element 33, the processor 31 performs the processing sequence illustrated in FIG. 4, thereby setting a control target value. According to the present example, furthermore, either one of three functions illustrated in FIG. 10 that represents the relationship between displacements c as a parameter and control target values, for example, is used in setting a control target value. In FIG. 10, the horizontal axis represents the displacements c of the elongate member 23A and the vertical axis the output electric power P in the constant electric power control process, the target temperature T in the temperature control process, and/or the target amplitude A in the vibration control process as a control target value.

With any of the functions illustrated in FIG. 10, the output electric power P, the target temperature T, and/or the target amplitude A set as a control target value increases continuously according to an increase in the displacement c acquired as a parameter. In other words, with any of the functions illustrated in FIG. 10, the output of the electric energy to the electric element 33 increases continuously according to an increase in the displacement ε. With the function indicated by the solid line in FIG. 10, the control target value increases linearly according to an increase in the displacement ε. With each of the function indicated by the broken line in FIG. 10 and the function indicated by the dot-and-dash line in FIG. 10, the control target value increases nonlinearly according to an increase in the displacement ε.

For example, in the case where the treatment target is gripped in the state where the bend angle, or the curvature angle, β is the first angle β1, the processor 31 acquires the first value ε1 as a parameter, and the amount F of the gripping force between the clamp members 17 and 18 becomes the first amount F1 of force. In the case where the treatment target is gripped in the state where the bend angle, or the curvature angle, β is the second angle β2 that is larger than the first angle β1, the processor 31 acquires the second value ε2 that is larger than the first value ε1 as a parameter, and the amount F of the gripping force between the clamp members 17 and 18 becomes the second amount F2 of force that is smaller than the first amount F1 of force. Assuming that a control target value is set using any of the functions illustrated in FIG. 10, in the case where the processor 31 acquires the second value ε2 as a parameter or displacement c, the processor 31 sets the output electric power P to a large value as a control target value and/or sets the target temperature T to a high value as a control value compared with the case in which the controller 31 acquires the first value ε1 as a parameter. Instead of or in addition to the setting described hereinbefore, in the case where the processor 31 acquires the second value ε2 as a parameter, the processor 31 may set the target amplitude A to a large value as a control target value compared with the case in which the controller 31 acquires the first value ε1 as a parameter.

Since the control target value is set as described hereinbefore, according to the present example, too, in the state where the bend angle β is large, such as the state where the displacement ε is of the second value ε2 or the like, the control target value that is set is large and the output of the electric energy to the electric element 33 increases compared with the state where the bend angle β is small or 0°, such as the state where the displacement ε is of the first value ε1 or the like. Furthermore, since the control target value is set as described hereinbefore, according to the present example, too, in the state where the amount F of the gripping force is small, such as the state where the amount F of the gripping force is the second amount F2 of force or the like, the control target value that is set is large and the output of the electric energy to the electric element 33 increases compared with the state where the amount F of the gripping force is large, such as the state where the amount F of the gripping force is the first amount F1 of force or the like. Therefore, the present example operates in the same way and offers the same advantages as the first example. Specifically, the output of the electric energy is adjusted according to the amount F of the gripping force, allowing the treatment target to be appropriately treated by the treatment energy, even though the amount F of the gripping force varies due to bending or curving of the end effector 8.

According to an example, the sensor 37 detects the position of the elongate member 23B rather than the elongate member 23A, and the processor 31 acquires a displacement of the elongate member 23B from the neutral position as a parameter. According to another example, the sensor 37 detects the positions of both the elongate members 23A and 23B, and the processor 31 acquires displacements of the elongate members 23A and 23B from the neutral position as a parameter. According to an example, the sensor 37 detects the portion or the angular position of the operating member 25 through which an operation to move the elongate members 23A and 23B is entered. Then, the processor 31 acquires a displacement or an angular displacement of the operating member 25 from the neutral state as a parameter based on the detected result from the sensor 37. According to an arrangement in which a drive force is transmitted from the operating member 25 through separate members to the elongate members 23A and 23B, the sensor 37 may detect the position or the angular position of either one of the members between the operating member 25 and the elongate members 23A and 23B. In this case, the processor 31 acquires a displacement or an angular displacement of the member whose position or angular position is detected by the sensor 37 from the neutral state as a parameter.

Therefore, according to the second example and the examples related thereto, based on the detected result from the sensor 37, the processor 31 acquires, as a parameter, a displacement or an angular displacement from the neutral position of the member (23A; 23B; 25) that transmits a drive force to bent or curve the end effector 8 to the end effector 8. According to the examples related to the second example, too, the parameter acquired by the processor 31 varies according to a bent state or a curved state of the end effector 8 and is related to the amount F of the gripping force between the clamp members 17 and 18. Since a control target value is set based on the acquired parameter as with the second example, these examples operate in the same way and offer the same advantages as the second example.

According to an example, in the case where a displacement or an angular displacement from the neutral position of the member (23A; 23B; 25) to which there is transmitted a drive force to bent or curve the end effector 8 is acquired as a parameter, a control target value may be set using a table or the like similar to the table illustrated in FIG. 7. According to another example, in the case where a bend angle, or a curvature angle, β of the end effector 8 is acquired as a parameter, a control target value may be set using functions or the like similar to the functions illustrated in FIG. 10.

Third Example

Figure 11:
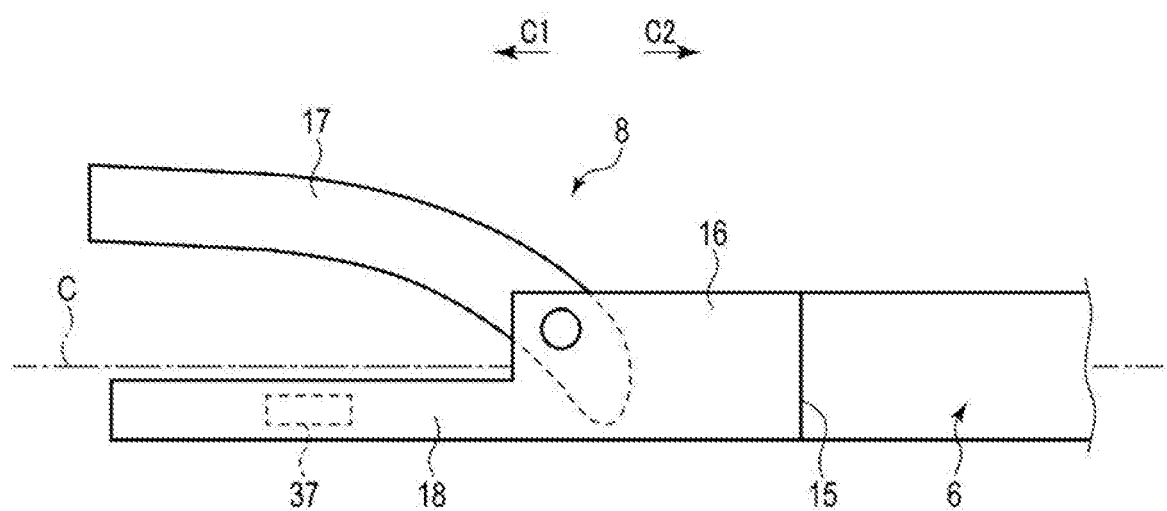
FIG. 11 is a schematic view illustrating a sensor according to a third example.

According to a third example illustrated in FIG. 11, a pressure sensor is mounted as the sensor 37 on the clamp member 18. The pressure sensor is disposed in the clamp member 18 or on a surface of the clamp member 18 that is opposite the side where the clamp member 17 is positioned. The pressure sensor may be a known sensor such as a strain gage, an electrostatic capacitance sensor, a resistive film sensor, or the like, for example. According to the present example, the sensor 37 detects a pressure p acting on the clamp member 18 as a detection target. The processor 31 acquires the pressure p acting on the clamp member 18 as a parameter based on the detected result from the sensor 37. At this time, the processor 31 acquires the detection target detected by the sensor 37 as a parameter.

Figure 12:
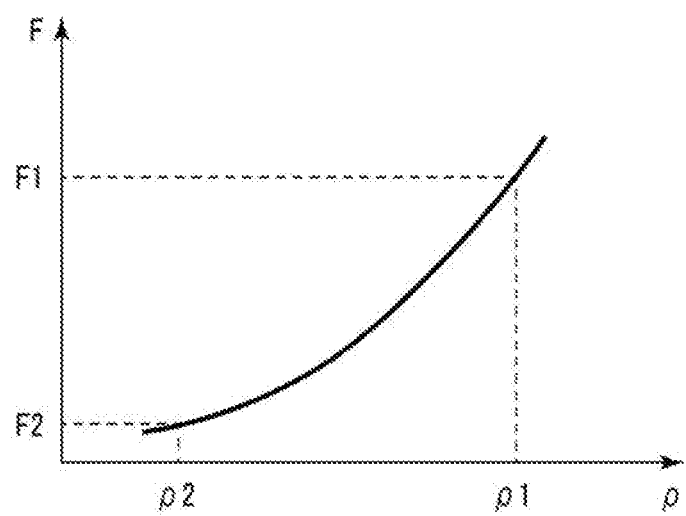
FIG. 12 is a schematic diagram illustrating by way of example the relationship between pressures acting on one of clamp members and amounts of a gripping force between the clamp members.

FIG. 12 illustrates by way of example the relationship between pressures p acting on the clamp member 18 and amounts F of a gripping force between the clamp members 17 and 18. In FIG. 12, the horizontal axis represents the pressures p and the vertical axis the amounts F of the gripping force. In the state where the treatment target is gripped between the clamp members 17 and 18, the pressure ρ on the clamp member 18 varies according to the amount F of the gripping force between the clamp members 17 and 18. As illustrated in FIG. 12, the larger the amount F of the gripping force is, the larger the pressure ρ on the clamp member 18 is. Therefore, the pressure ρ on the clamp member 18 acts as a parameter that is affected by the amount F of the gripping force between the clamp members 17 and 18 and that is related to the amount F of the gripping force. Furthermore, as described hereinbefore, when the bent state or curved state of the end effector 8 varies, the amount F of the gripping force between the clamp members 17 and 18 varies. Consequently, the pressure ρ acting on the clamp member 18 acts as a parameter that varies according to the bent state or the curved state of the end effector 8.

For example, in the case where the relationship illustrated in FIG. 12 is established, the processor 31 acquires a first value (ρ1) in the state where the amount F of the gripping force between the clamp members 17 and 18 becomes the first amount F1 of force. Moreover, the processor 31 acquires a second value (ρ2) that is smaller than the first value (ρ1) as a parameter in the state where the amount F of the gripping force between the clamp members 17 and 18 becomes the second amount F2 of force that is smaller than the first amount F1 of force.

According to the present example, after the treatment target is gripped between the clamp members 17 and 18 and before electric energy starts to be output to the electric element 33, the processor 31 performs the processing sequence illustrated in FIG. 4, thereby setting a control target value. According to the present example, furthermore, a table illustrated in FIG. 13 that illustrates the relationship between pressures p as a parameter and control target values, for example, is used in setting a control target value. According to the relationship represented by the table illustrated in FIG. 13, the output electric power P, the target temperature T, and/or the target amplitude A set as a control target value decreases stepwise at each of threshold values ρa, ρb, and ρc according to an increase in the pressure ρ acquired as a parameter. According to the relationship represented by the table illustrated in FIG. 13, therefore, the output of the electric energy to the electric element 33 decreases stepwise at each of the threshold values ρa, ρb, and ρc according to an increase in the pressure p.

For example, in the case where the amount F of the gripping force between the clamp members 17 and 18 becomes the first amount F1 of force due to the bent state or the curved state, the processor 31 acquires the first value ρ1 that is equal to or larger than the threshold value ρc as a parameter. In this case, the processor 31 sets the output electric power P as a control target value to an electric power P1 and/or sets the target temperature T as a control target value to a temperature T1 based on the table illustrated in FIG. 13. At this time, instead of or in addition to the setting described hereinbefore, the processor 31 may set the target amplitude A as a control target value to an amplitude A1. Moreover, in the case where the amount F of the gripping force between the clamp members 17 and 18 becomes the second amount F2 of force that is smaller than the first amount F1 of force due to the bent state or curved state, the processor 31 acquires the second value ρ2 that is smaller than the threshold value ρa as a parameter. In this case, the processor 31 sets the output electric power P as a control target value to an electric power P4 that is larger than the electric power P1 based on the table illustrated in FIG. 13, and/or sets the target temperature T as a control target value to a temperature T4 that is higher than the temperature T1. At this time, instead of or in addition to the setting described hereinbefore, the processor 31 may set the target amplitude A as a control target value to an amplitude A4 that is larger than the amplitude A1.

Since the control target value is set as described hereinbefore, according to the present example, too, in the state where the amount F of the gripping force is small, such as the state where the pressure ρ is of the second value ρ2 or the like, the control target value that is set is large and the output of the electric energy to the electric element 33 increases compared with the state where the amount F of the gripping force is large, such as the state where the pressure ρ is of the first value ρ1 or the like. Therefore, the present example operates in the same way and offers the same advantages as the example described hereinbefore. Specifically, the output of the electric energy is adjusted according to the amount F of the gripping force, allowing the treatment target to be appropriately treated by the treatment energy, even though the amount F of the gripping force varies due to bending or curving of the end effector 8.

According to an example, the sensor 37 detects a pressure on the clamp member 17 instead of the clamp member 18, and the processor 31 acquires the pressure acting on the clamp member 17 as a parameter. According to another example, the sensor 37 detects respective pressures on both of the clamp members 17 and 18, and the processor 31 acquires the respective pressures on the clamp members 17 and 18 as a parameter. According to these examples, the parameter acquired by the processor 31 varies according to a bent state or a curved state of the end effector 8 and is related to the amount F of the gripping force between the clamp members 17 and 18. Since a control target value is set based on the acquired parameter as with the third example, these examples operate in the same way and offer the same advantages as the third example.

Figures 13, 14:
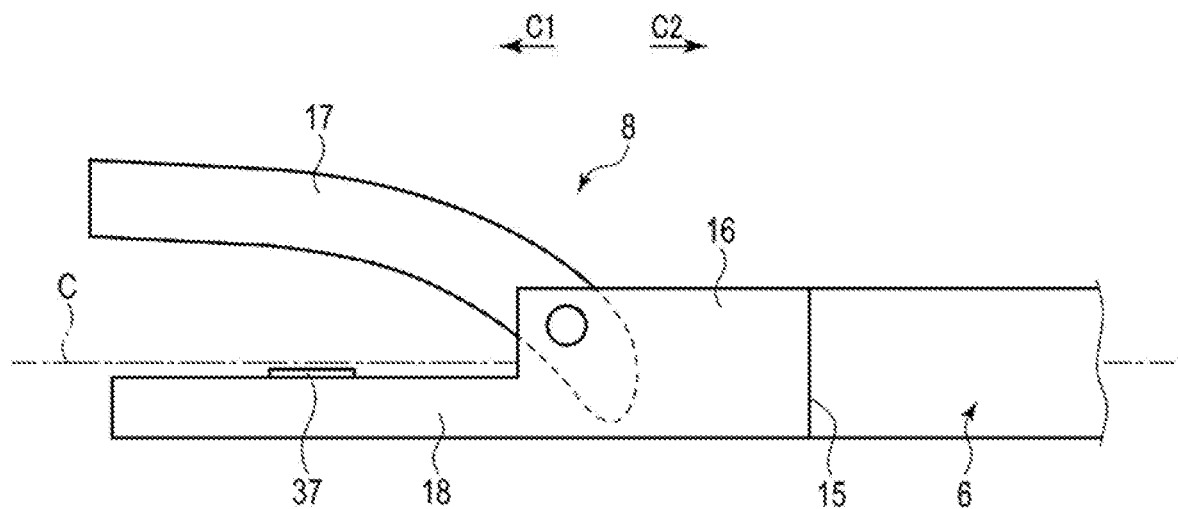
FIG. 13 is a schematic diagram illustrating by way of example a table used in setting a control target value based on a parameter, i.e., a pressure acting on the clamp member, according to the third example.
FIG. 14 is a schematic view illustrating a sensor according to a fourth example.

According to an example, in the case where the pressure on either one of the clamp members 17 and 18 is acquired as a parameter, a control target value may be set using functions instead of the table illustrated in FIG. 13 or the like. In this case, with the functions that are used, the control target value decreases continuously according to an increase in the pressure acquired as a parameter.

Fourth Example

According to a fourth example illustrated in FIG. 14, a gap sensor is mounted as the sensor 37 on the end effector 8. The gap sensor is disposed on a region of the clamp member 17 that faces the clamp member 18 or on a region of the clamp member 18 that faces the clamp member 17. The gap sensor may be a known sensor such as an optical sensor, an electrostatic capacitance sensor, or the like, for example. According the present example, the sensor 37 detects a gap, or a distance, g between the clamp members 17 and 18 as a detection target. The processor 31 acquires the gap g between the clamp members 17 and 18 as a parameter based on the detected result from the sensor 37. At this time, the processor 31 acquires the detection target detected by the sensor 37 as a parameter.

Figure 15:
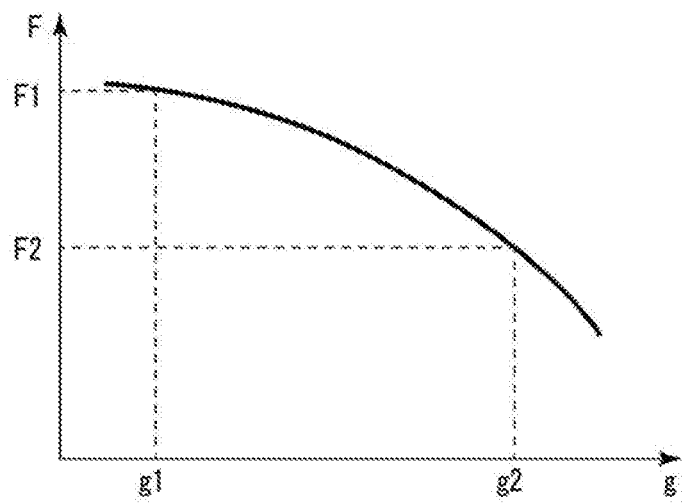
FIG. 15 is a schematic diagram illustrating by way of example the relationship between gaps between clamp members and amounts of a gripping force between the clamp members.

FIG. 15 illustrates by way of example the relationship between gaps g between the clamp members 17 and 18 and amounts F of a gripping force between the clamp members 17 and 18. In FIG. 15, the horizontal axis represents the gaps g and the vertical axis the amounts F of the gripping force. In the state where the treatment target is gripped between the clamp members 17 and 18, the gap g between the clamp members 17 and 18 affects the amount F of the gripping force between the clamp members 17 and 18. As illustrated in FIG. 15, the larger the gap g between the clamp members 17 and 18 is, the smaller the amount F of the gripping force is. Therefore, the gap g between the clamp members 17 and 18 acts as a parameter that is related to the amount F of the gripping force. Furthermore, when the bent state or the curved state of the end effector 8 varies, since the axial force from the drive shaft 21 to the end effector 8 varies as described hereinbefore, the gap g between the clamp members 17 and 18 with the treatment target gripped therebetween varies. Therefore, the gap g between the clamp members 17 and 18 acts as a parameter that varies according to a bent state or a curved state of the end effector 8.

For example, in the case where the relationship illustrated in FIG. 15 is established, the processor 31 acquires a first value (g1) as a parameter, or a gap g, in the state where the amount F of the gripping force between the clamp members 17 and 18 becomes the first amount F1 of force. Moreover, the processor 31 acquires a second value (g2) that is larger than the first value (g1) as a parameter in the state where the amount F of the gripping force between the clamp members 17 and 18 becomes the second amount F2 of force that is smaller than the first amount F1 of force.

Figure 16:
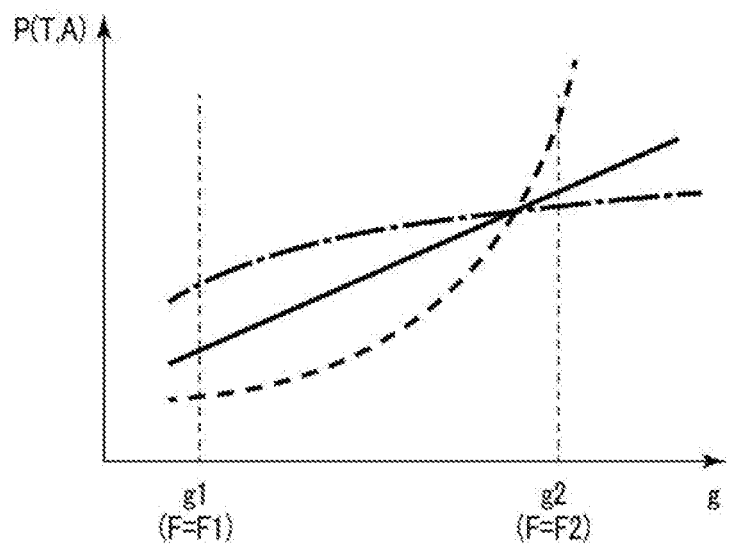
FIG. 16 is a schematic diagram illustrating by way of example a function used in setting a control target value based on a parameter, i.e., a gap between clamp members.

According to the present example, too, after the treatment target is gripped between the clamp members 17 and 18 and before electric energy starts to be output to the electric element 33, the processor 31 performs the processing sequence illustrated in FIG. 4, thereby setting a control target value. According to the present example, furthermore, either one of three functions illustrated in FIG. 16 that represents the relationship between gaps g as a parameter and control target values, for example, is used in setting a control target value. In FIG. 16, the horizontal axis represents the gaps g between the clamp members 17 and 18 and the vertical axis the output electric power Pin the constant electric power control process, the target temperature T in the temperature control process, and/or the target amplitude A in the vibration control process as a control target value.

With any of the functions illustrated in FIG. 16, the control target value increases continuously and the output of the electric energy to the electric element 33 increases continuously according to an increase in the gap g acquired as a parameter. With the function indicated by the solid line in FIG. 16, the control target value increases linearly according to an increase in the gap g. With each of the function indicated by the broken line in FIG. 16 and the function indicated by the dot-and-dash line in FIG. 16, the control target value increases nonlinearly according to an increase in the gap g.

For example, in the case where the gap g becomes the first value g1 due to the bent state or curved state, the processor 31 acquires the first value ε1 as a parameter, and the amount F of the gripping force between the clamp members 17 and 18 becomes the first amount F1 of force. In the case where the gap g becomes the second value g2 that is larger than the first value g1 due to the bent state or the like, the processor 31 acquires the second value g2 that is larger than the first value g1 as a parameter, and the amount F of the gripping force between the clamp members 17 and 18 becomes the second amount F2 of force that is smaller than the first amount F1 of force. Assuming that a control target value is set using any of the functions illustrated in FIG. 16, in the case where the processor 31 acquires the second value g2 as a parameter, or a gap g, the processor 31 sets the control target value to a large value compared with the case in which the controller 31 acquires the first value g1 as a parameter.

Since the control target value is set as described hereinbefore, according to the present example, too, in the state where the amount F of the gripping force is small, such as the state where the gap g is of the second value g2 or the like, the control target value that is set is large and the output of the electric energy to the electric element 33 increases compared with the state where the amount F of the gripping force is large, such as the state where the gap g is of the first value g1 or the like. Therefore, the present example operates in the same way and offers the same advantages as the example described hereinbefore. Specifically, the output of the electric energy is adjusted according to the amount F of the gripping force, allowing the treatment target to be appropriately treated by the treatment energy, even though the amount F of the gripping force varies due to bending or curving of the end effector 8.

According to an example, in the case where the gap g between the clamp members 17 and 18 is acquired as a parameter, a control target value may be set using a table instead of the functions illustrated in FIG. 16 or the like. In this case, with the table that is used, the control target value increases stepwise at each of the threshold values according to an increase in the gap g acquired as a parameter.

Fifth Example

Figure 17:
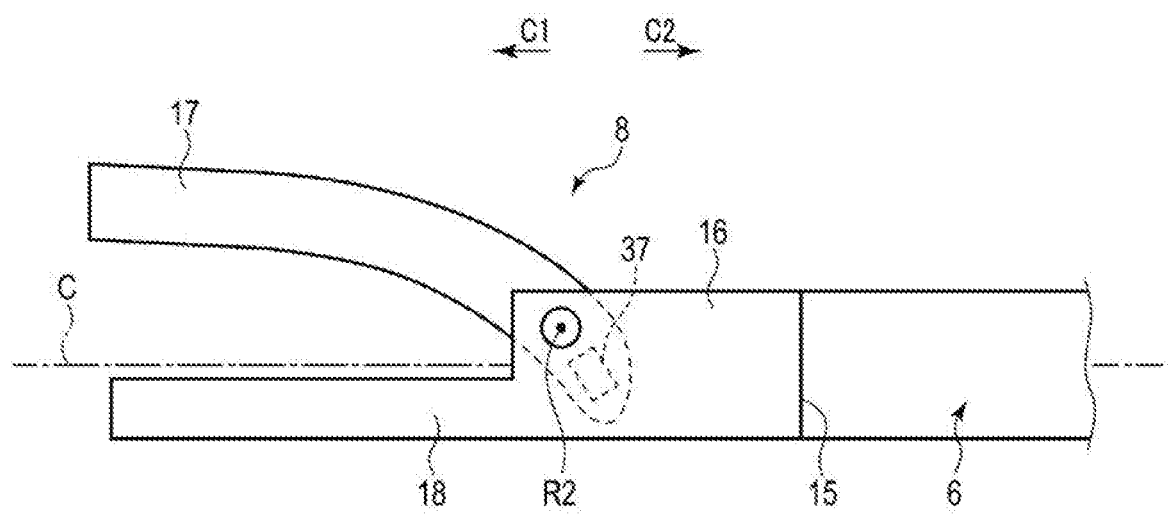
FIG. 17 is a schematic view illustrating a sensor according to a fifth example.

According to a fifth example illustrated in FIG. 17, one of the clamp members 17 and 18 is angularly movable with respect to the effector body 16 about a turn axis R2, and an angle sensor is mounted as the sensor 37 on a clamp member, e.g., the clamp member 17, that angularly moves about the turn axis R2. The angle sensor may be the known sensor described hereinbefore, for example. According to the present example, the sensor 37 detects an angular position of the angularly moving clamp member, e.g., the clamp member 17, about the turn axis R2 as a detection target. Moreover, while the clamp members 17 and 18 are being closed with respect to each other, the detected result from the sensor 37 is continuously transmitted to the processor 31. The processor 31 calculates and acquires a change α in the angle between the clamp members 17 and 18 in the closing movement of the clamp members 17 and 18 based on the detected result from the sensor 37.

According to the example in which both of the clamp members 17 and 18 are angularly movably mounted on the effector body 16, the sensor 37 detects respective angular positions of the clamp members 17 and 18 about the turn axis R2. Also in this case, the processor 31 calculates and acquires a change α in the angle between the clamp members 17 and 18 in the closing movement of the clamp members 17 and 18 based on the detected result from the sensor 37.

As described hereinbefore, when the end effector 8 is bent or curved with respect to the sheath 6, the distal-end portion of the drive shaft 21 is bent or curved. When the distal-end portion of the drive shaft 21 is bent or curved at the link mechanism 22 or the like, the length of a region of the drive shaft 21 that passes between the end effector 8 and the sheath 6 varies with respect to the neutral state. When the length of the region of the drive shaft 21 that passes between the end effector 8 and the sheath 6 varies, the relative positions of the clamp members 17 and 18 with respect to each other vary, so that the change α in the angle between the clamp members 17 and 18 in the closing movement of the clamp members 17 and 18 varies. Therefore, the change α in the angle between the clamp members 17 and 18 in their closing movement acts as a parameter that varies according to the bent state or the curved state of the end effector 8.

Figure 18:
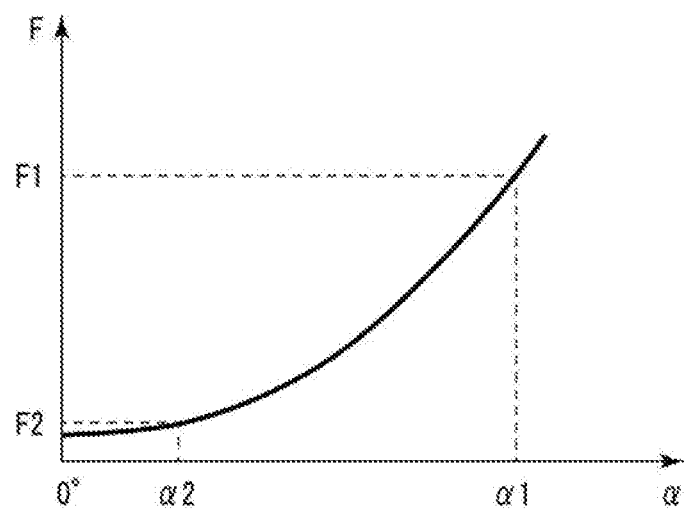
FIG. 18 is a schematic diagram illustrating by way of example the relationship between changes in an angle between clamp members as the clamp members are closed and amounts of a gripping force between the clamp members.

FIG. 18 illustrates by way of example the relationship between changes α in the angle between the clamp members 17 and 18 in the closing movement of the clamp members 17 and 18 and amounts F of a gripping force between the clamp members 17 and 18. In FIG. 18, the horizontal axis represents the changes α in the angle and the vertical axis the amounts F of the gripping force. As illustrated in FIG. 18, when the clamp members 17 and 18 are closed with respect to each other to grip the treatment target therebetween, providing other conditions such as the size of the treatment target, etc. remain the same, the larger the change α in the angle between the clamp members 17 and 18 in their closing movement is, the larger the amount F of the gripping force between the clamp members 17 and 18 is. Therefore, the parameter acquired by the processor 31, i.e., the change α in the angle between the clamp members 17 and 18 in the closing movement of the clamp members 17 and 18, acts as a parameter that affects the amount F of the gripping force between the clamp members 17 and 18 and that is related to the amount F of the gripping force.

For example, in the case where the relationship illustrated in FIG. 18 is established, in the state where the change α in the angle between the clamp members 17 and 18 becomes a first value α1 and the processor 31 acquires the first value (α1) as a parameter, the amount F of the gripping force between the clamp members 17 and 18 becomes the first amount F1 of force. Furthermore, in the state where the change α in the angle between the clamp members 17 and 18 becomes a second angle α2 that is smaller than the first value α1 and the processor 31 acquires the second value (α2) as a parameter, the amount F of the gripping force between the clamp members 17 and 18 becomes the second amount F2 of force that is smaller than the first amount F1 of force.

According to the present example, when the clamp members 17 and 18 start to be closed, the processor 31 starts the processing sequence illustrated in FIG. 4, setting a control target value prior to starting the output of the electric energy to the electric element 33. According to the present example, furthermore, a table illustrated in FIG. 19 that illustrates the relationship between angle changes α as a parameter and control target values, for example, is used in setting a control target value. According to the relationship represented by the table illustrated in FIG. 19, the output electric power P, the target temperature T, and/or the target amplitude A set as a control target value decreases stepwise at each of threshold values αa, αb, αc according to an increase in the angle change α acquired as a parameter. According to the relationship represented by the table illustrated in FIG. 19, therefore, the output of the electric energy to the electric element 33 decreases stepwise at each of the threshold values αa, αb, αc according to an increase in the angle change α.

For example, in the case where the angle change α in the closing movement of the clamp members 17 and 18 becomes the first value α1 due to a bent state or a curved state and the amount F of the gripping force between the clamp members 17 and 18 becomes the first amount F1 of force, the processor 31 acquires the first value α1 that is equal to or larger than the threshold value αc as a parameter. In this case, the processor 31 sets the output electric power P as a control target value to an electric power P1 and/or sets the target temperature T as a control target value to a temperature T1 based on the table illustrated in FIG. 19. At this time, instead of or in addition to the setting described hereinbefore, the processor 31 may set the target amplitude A as a control target value to an amplitude A1. Moreover, in the case where the angle change α in the closing movement of the clamp members 17 and 18 becomes the second value α2 that is smaller than the first value α1 due to a bent state or a curved state and the amount F of the gripping force between the clamp members 17 and 18 becomes the second amount F2 of force that is smaller than the first amount F1 of force, the processor 31 acquires the second value α2 that is smaller than the threshold value αa as a parameter. In this case, the processor 31 sets the output electric power P as a control target value to an electric power P4 that is larger than the electric power P1 and/or sets the target temperature T as a control target value to a temperature T4 that is higher than the temperature T1 based on the table illustrated in FIG. 19. At this time, instead of or in addition to the setting described hereinbefore, the processor 31 may set the target amplitude A as a control target value to an amplitude A4 that is larger than the amplitude A1.

Since the control target value is set as described hereinbefore, according to the present example, too, in the state where the amount F of the gripping force is small, such as the state where the angle change α is of the second value α2 or the like, the control target value that is set is large and the output of the electric energy to the electric element 33 increases compared with the state where the amount F of the gripping force is large, such as the state where the angle change α is of the first value α1 or the like. Therefore, the present example operates in the same way and offers the same advantages as the example described hereinbefore. Specifically, the output of the electric energy is adjusted according to the amount F of the gripping force, allowing the treatment target to be appropriately treated by the treatment energy, even though the amount F of the gripping force varies due to bending or curving of the end effector 8.

Figures 19, 20:
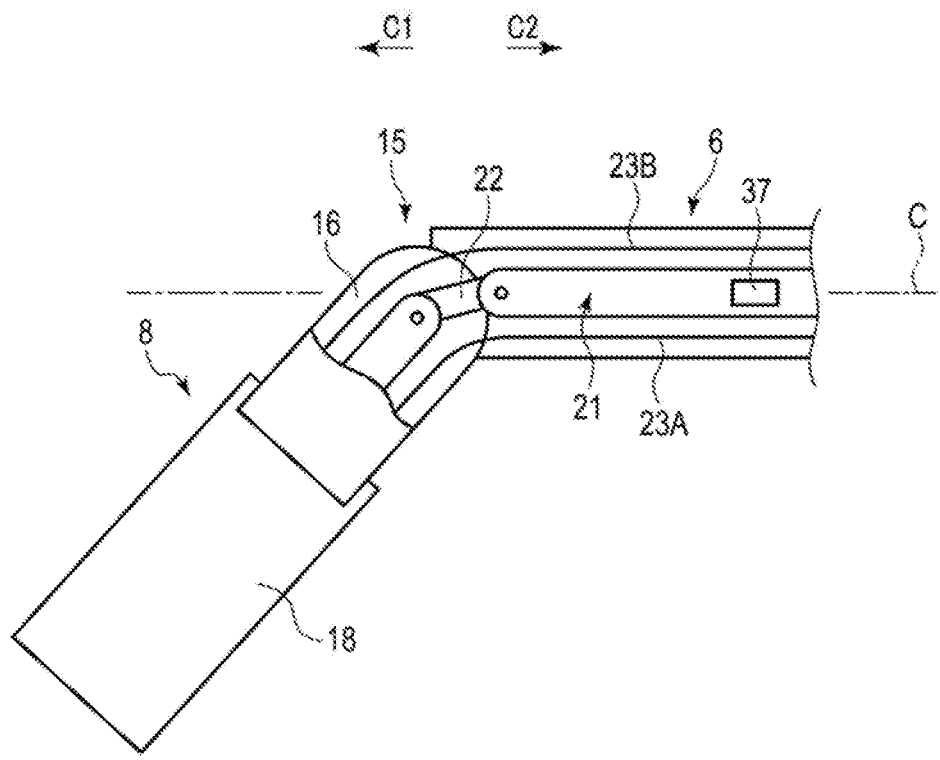
FIG. 19 is a schematic diagram illustrating by way of example a table used in setting a control target value based on a parameter, i.e., a change in the angle between clamp members as the clamp members are closed, according to the fifth example.
FIG. 20 is a schematic view illustrating a sensor according to a sixth example.

According to an example, in the case where the angle change α in the closing movement of the clamp members 17 and 18 is acquired as a parameter, a control target value may be set using functions instead of the table illustrated in FIG. 19 or the like. In this case, with the functions that are used, the control target value decreases continuously according to an increase in the angle change α acquired as a parameter.

Sixth Example

According to a sixth example illustrated in FIG. 20, a positional sensor is mounted as the sensor 37 on the drive shaft 21. The sensor 37 is disposed on the proximal-end side of the bending joint 15, for example, in any states. Specifically, the sensor 37 is positioned on the proximal-end side with respect to the distal end of the sheath 6 in any states. The positional sensor be the known sensor described hereinbefore, for example. According to the present example, the sensor 37 detects a position of the drive shaft 21 with respect to the sheath 6 as a detection target. Furthermore, while the drive shaft 21 is moved or operated in ganged relation to the closing movement of the clamp members 17 and 18, the detected result from the sensor 37 is continuously transmitted to the processor 31. The processor 31 then calculates and acquires an amount η of movement of the drive shaft 21 with respect to the sheath 6 in ganged relation to the closing movement of the clamp members 17 and 18 based on the detected result from the sensor 37. At this time, an amount η of movement of the drive shaft 21 in a direction along the longitudinal axis C, for example, is acquired.

As described hereinbefore, when the end effector 8 is bent or curved with respect to the sheath 6, the length of a region of the drive shaft 21 that passes between the end effector 8 and the sheath 6 varies with respect to the neutral state. When the length of the region of the drive shaft 21 that passes between the end effector 8 and the sheath 6 varies, the position of the drive shaft 21 with respect to the sheath 6 varies in a region of the sheath 6 on the proximal-end side with respect to the distal end thereof. Consequently, as the length of the region of the drive shaft 21 that passes between the end effector 8 and the sheath 6 varies, the amount η of movement of the drive shaft 21 in ganged relation to the closing movement of the clamp members 17 and 18 varies. Therefore, the amount η of movement of the drive shaft 21 in ganged relation to the closing movement of the clamp members 17 and 18 acts as a parameter that varies according to a bent state or a curved state of the end effector 8.

Figure 21:
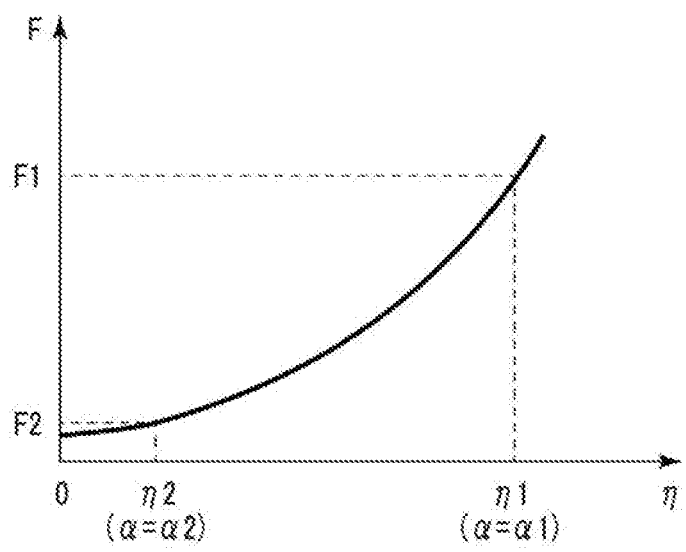
FIG. 21 is a schematic diagram illustrating by way of example the relationship between amounts by which a drive shaft is moved in ganged relation to the closing motion of clamp members and amounts of a gripping force between the clamp members.

FIG. 21 illustrates by way of example the relationship between amounts η of movement of the drive shaft 21 in ganged relation to the closing movement of the clamp members 17 and 18 and amounts F of a gripping force between the clamp members 17 and 18. In FIG. 21, the horizontal axis represents the amounts η of movement and the vertical axis the amounts F of the gripping force. When the clamp members 17 and 18 are closed with respect to each other to grip the treatment target therebetween, providing other conditions remain the same, the larger the amount η of movement of the drive shaft 21 is, the larger the change α in the angle between the clamp members 17 and 18 in their closing movement is. Therefore, as illustrated in FIG. 21, providing the other conditions remain the same, the larger the amount η of movement of the drive shaft 21 is, the larger the amount F of the gripping force between the clamp members 17 and 18 is. Therefore, the parameter acquired by the processor 31, i.e., the amount η of movement of the drive shaft 21 in ganged relation to the closing movement of the clamp members 17 and 18, acts as a parameter that affects the amount F of the gripping force between the clamp members 17 and 18 and that is related to the amount F of the gripping force.

For example, in the case where the relationship illustrated in FIG. 21 is established, in the state where the processor 31 acquires a first value η1 as the amount η of movement of the drive shaft 21, the angle change α between the clamp members 17 and 18 is of the first change α1 and the amount F of the gripping force between the clamp members 17 and 18 is the first amount F1 of force. Furthermore, in the case where the processor 31 acquires a second value η2 that is smaller than the first value η1 as the amount η of movement of the drive shaft 21, the angle change α between the clamp members 17 and 18 is of the second change α2 that is smaller than the first change α1 and the amount F of the gripping force between the clamp members 17 and 18 is the second amount F2 of force that is smaller than the first amount F1 of force.

Figure 22:
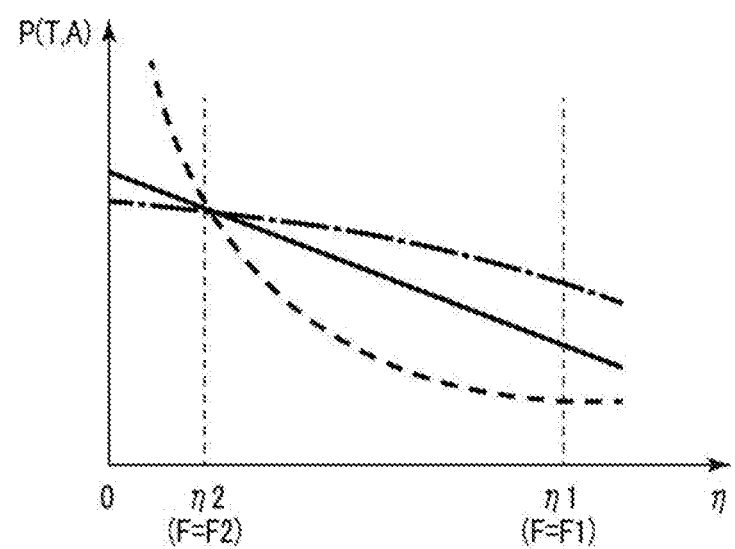
FIG. 22 is a schematic diagram illustrating by way of example a function used in setting a control target value based on a parameter, i.e., an amount by which a drive shaft is moved in ganged relation to the closing motion of the clamp members, according to the sixth example.

According to the present example, when the drive shaft 21 starts to operate in ganged relation to the closing movement of the clamp members 17 and 18, the processing sequence illustrated in FIG. 4 is started by the processor 31 prior to the output of the electric energy to the electric element 33. According to the present example, furthermore, either one of three functions illustrated in FIG. 22 that represents the relationship between amounts η of movement as a parameter and control target values, for example, is used in setting a control target value. In FIG. 22, the horizontal axis represents the amounts η of movement of the drive shaft 21 and the vertical axis the output electric power P in the constant electric power control process, the target temperature T in the temperature control process, and/or the target amplitude A in the vibration control process as a control target value.

With any of the functions illustrated in FIG. 22, the control target value decreases continuously and the output of the electric energy to the electric element 33 decreases continuously according to an increase in the amount η of movement acquired as a parameter. With the function indicated by the solid line in FIG. 22, the control target value decreases linearly according to an increase in the amount η of movement. With each of the function indicated by the broken line in FIG. 22 and the function indicated by the dot-and-dash line in FIG. 22, the control target value decreases nonlinearly according to an increase in the amount η of movement.

For example, in the case where the amount η of movement becomes the first value η1 and the angle change α becomes the first change α1 due to the bent state or curved state, the processor 31 acquires the first value η1 as a parameter, and the amount F of the gripping force between the clamp members 17 and 18 becomes the first amount F1 of force. In the case where the amount η of movement becomes the second value η2 that is smaller than the first value η1 and the angle change α becomes the second change α2 that is smaller than the first change α1 due to the bent state or the like, the processor 31 acquires the second value η2 as a parameter, and the amount F of the gripping force between the clamp members 17 and 18 becomes the second amount F2 of force that is smaller the first amount F1 of force. Assuming that a control target value is set using any of the functions illustrated in FIG. 22, in the case where the processor 31 acquires the second value η2 as a parameter, or amount η of movement of the drive shaft 21, the processor 31 sets the control target value to a large value compared with the case in which the controller 31 acquires the first value η1 as a parameter.

Since the control target value is set as described hereinbefore, according to the present example, too, in the state where the amount F of the gripping force is small, such as the state where the amount η of movement is of the second value η2 or the like, the control target value that is set is large and the output of the electric energy to the electric element 33 increases compared with the state where the amount F of the gripping force is large, such as the state where the amount η of movement is of the first value η1 or the like. Therefore, the present example operates in the same way and offers the same advantages as the example described hereinbefore. Specifically, the output of the electric energy is adjusted according to the amount F of the gripping force, allowing the treatment target to be appropriately treated by the treatment energy, even though the amount F of the gripping force varies due to bending or curving of the end effector 8.

According to an example, in the case where the amount η of movement of the drive shaft 21 that operates in ganged relation to the closing movement of the clamp members 17 and 18 is acquired as a parameter, a control target value may be set using a table instead of the functions illustrated in FIG. 22 or the like. In this case, with the table that is used, the control target value decreases stepwise at each of the threshold values according to an increase in the amount η of movement acquired as a parameter.

Modification of the Sixth Example

Figure 23:
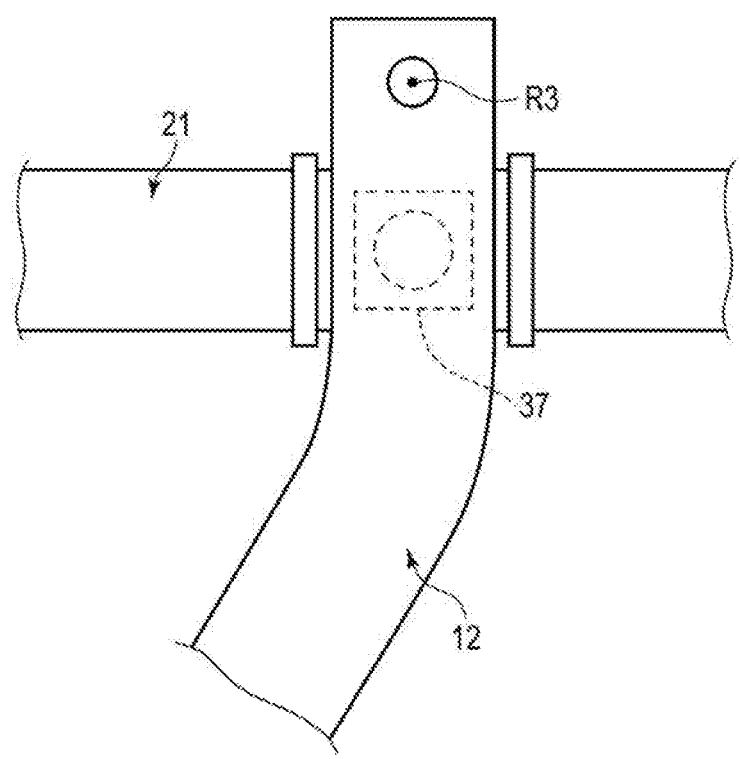
FIG. 23 is a schematic view illustrating a sensor according to a modification of the sixth example.

According to a modification of the sixth example illustrated in FIG. 23, the handle 12 is angularly movable about a turn axis R3 with respect to the housing 7, and an angle sensor is mounted as the sensor 37 on the handle 12. The angle sensor may be the known sensor described hereinbefore, for example. According to the present example, the sensor 37 detects an angular position of the handle 12 about the turn axis R3 as a detection target. While the handle 12 is angularly moved or operated in ganged relation to the closing movement of the clamp members 17 and 18 with respect to each other, the detected result from the sensor 37 is continuously transmitted to the processor 31. Then, the processor 31 calculates and acquires, as a parameter, an angle change η' of the handle 12 about the turn axis R3 as the handle 12 is angularly moved or operated in ganged relation to the closing movement of the clamp members 17 and 18, based on the detected result from the sensor 37.

As described hereinbefore, when the end effector 8 is bent or curved with respect to the sheath 6, the position of the drive shaft 21 with respect to the sheath 6 varies with respect to the neutral state. Furthermore, as described hereinbefore, the handle 12 is coupled to the drive shaft 21, and the drive force to open or close the clamp members 17 and 18 with respect to each other is transmitted from the handle 12 to the drive shaft 21. Therefore, as the position of the drive shaft 21 with respect to the sheath 6 varies, the angular position of the handle 12 about the turn axis R3 varies. As the angular position of the handle 12 varies, the angle change η' of the handle 12 in ganged relation to the closing movement of the clamp members 17 and 18 varies. Therefore, the parameter acquired by the processor 31, i.e., the angle change η' of the handle 12 in ganged relation to the closing movement of the clamp members 17 and 18 acts as a parameter that varies according to the bent state or curved state of the end effector 8.

When the clamp members 17 and 18 are closed with respect to each other to grip the treatment target therebetween, providing other conditions remain the same, since the larger the angle change η' of the handle 12 is, the larger the amount η of movement of the drive shaft 21 is, the angle change α between the clamp members 17 and 18 in their closing movement is large. Therefore, providing the other conditions remain the same, the larger the angle change η' of the handle 12 is, the larger the amount F of the gripping force between the clamp members 17 and 18. Therefore, the parameter acquired by the processor 31, i.e., the angle change η' of the handle 12 in ganged relation to the closing movement of the end effector 8 acts as a parameter that affects the amount F of the gripping force between the clamp members 17 and 18 and that is related to the amount F of the gripping force.

According to the present modification, a control target value is set in the same manner as the sixth example in which the amount η of movement of the drive shaft 21 is acquired as a parameter. Consequently, the present modification operates in the same way and offers the same advantages as the sixth example.

According to an arrangement in which a drive force to open or close the clamp members 17 and 18 is transmitted from the handle 12 through separate members to the drive shaft 21, the sensor 37 may detect the position or the angular position of either one of the members between the handle 12 and the drive shaft 21. In this case, the processor 31 acquires an amount of movement or angle change in an operation of the member, whose position or angular position is detected by the sensor 37, in ganged relation to the closing movement of the clamp members 17 and 18, as a parameter.

According to the sixth example and the modification, as described hereinbefore, the processor 31 acquires an amount of movement or angle change in an operation, in ganged relation to the closing movement of the clamp members 17 and 18, of the member (21; 12) that transmits a drive force to open or close the clamp members 17 and 18 with respect to each other, as a parameter based on the detected result from the sensor 37. According to these examples and the modification, the parameter acquired by the processor 31 varies according to the bent state or the curved state of the end effector 8 and is related to the amount F of the gripping force between the clamp members 17 and 18. According to these examples and the modification, since a control target value is set based on the acquired parameter in the same manner as with the sixth example, they operate in the same way and offer the same advantages as the sixth example.

Common Arrangement of the Embodiments Described Hereinbefore

According to the embodiments described hereinbefore, etc., the processor 31 acquires a parameter (β; ε; ρ; g; α; η; η') that varies according to a bent state or a curved state of the end effector (8) with respect to the sheath (6) and that is related to the amount (F) of the gripping force between the clamp members (17, 18). Then, the processor 31 sets a control target value for the control of the output of the electric energy to the electric element 33 based on the acquired parameter (β; ε; ρ; g; α; η; η').

The disclosed technology is not limited to the embodiments described hereinbefore, but various modifications may be made therein without departing from the scope of the invention when it is reduced to practice. The embodiments may be appropriately combined as much as possible, and the combinations offer combined advantages. Furthermore, the embodiments include inventions in various stages, and various inventions can be extracted by appropriately combining a plurality of components that are disclosed.

In sum, the disclosed technology is directed to a treatment system comprises a power supply device and a treatment tool configured to communicate electrically with the power supply device so as to perform an operation on a treatment target. The treatment tool includes a sheath and an end effector configured to detachably attach to the sheath and being capable of bending with respect to the sheath. The end effector includes an electric element used to apply a treatment energy to the treatment target using an electric energy. The power supply device includes a processor. The processor sets to increase an output of the electric energy to be supplied to the electric element at in a second state. The sheath and the end effector are bent at a predetermined angle with respect to one another, compared with a first state where the sheath and the end effector are disposed straight in line with one another.

The treatment system further comprises a pair of clamp members capable of being opened and closed with respect to one another. The processor acquires a parameter that varies according to the bent state of the end effector with respect to the sheath and is related to an amount of a gripping force between the clamp members and sets a control target value for controlling the electric energy based on the parameter. The processor acquires the parameter based on a detected result from a sensor disposed on the treatment tool. The processor acquires, as the parameter, a bend angle of the end effector with respect to the sheath. The treatment system further comprises an elongated member for transmitting a drive force to bend the end effector. The processor acquires, as the parameter, a displacement of the elongated member when the end effector changes from the first state to the second state. The treatment system further comprises an elongated member for transmitting a drive force to bend the end effector and an operating member for moving the elongate member.

The processor acquires, as the parameter, a displacement or a displaced angle of the operating member when the end effector changes from the first state to the second state. The processor acquires either a pressure acting on the clamp members or a gap between the clamp members as the parameter. The processor acquires, as the parameter, a change in an angle between the clamp members during closing movement of the clamp members. The processor acquires, as the parameter, an amount of movement or an angle change of a member for transmitting a drive force to open or close the clamp members with respect to one another, as the member operates in ganged relation to closing movement of the clamp members.

The processor acquires either an amount of movement of a drive shaft movable to open or close the clamp members with respect to one another, as the drive shaft operates in ganged relation to closing movement of the clamp members, or an angle change of a handle through which an operation input to open or close the clamp members with respect to one another is entered, as the handle operates in ganged relation to closing movement of the clamp members, as the amount of movement or the angle change. The processor acquires a first value as the parameter in a position where a bend angle of the end effector becomes a first angle, acquires a second value as the parameter in a position where the bend angle becomes a second angle that is larger than the first angle, and sets the control target value such that the output of the electric energy to the electric element is high in a position where the processor acquires the second value compared with a position in which the processor acquires the first value. The processor acquires a first value as the parameter in a position where the amount of the gripping force between the clamp members become a first amount of force, acquires a second value as the parameter in a position where the amount of the gripping force becomes a second amount of force that is smaller than the first amount of force, and sets the control target value such that the output of the electric energy to the electric element is high in a position where the processor acquires the second value compared with a position in which the processor acquires the first value.

Another aspect of the disclosed technology is directed to a treatment system comprises a power supply device and a treatment tool configured to communicate electrically with the power supply device so as to perform an operation on a treatment target. The treatment tool comprises a tubular sheath having respective distal and proximal ends. A housing is detachably attach to the proximal end and an end effector is configured to detachably attach to the distal end and being capable of bending with respect to the tubular sheath. The end effector includes a pair of clamp members capable of being opened and closed with respect to one another. The pair of clamp members includes an electric element used to apply a treatment energy to the treatment target gripped between the clamp members using an electric energy. The power supply device includes a processor that acquires a parameter that varies according to a bent state of the end effector with respect to the tubular sheath and being related to an amount of a gripping force between the clamp members, and sets a control target value for controlling an output of the electric energy to the electric element based on the acquired parameter.

The treatment system of claim further comprises a sensor for transmitting a detected result to the processor and the processor acquires the parameter based on the detected result from the sensor.

A further aspect of the disclosed technology is directed to a treatment tool comprises a housing. A tubular sheath having respective distal and proximal ends. The tubular sheath being detachably attached to the housing via the proximal end. An end effector is configured to detachably attach to the distal end and is capable of bending with respect to the tubular sheath. The end effector includes a pair of clamp members capable of being opened and closed with respect to one another. The pair of clamp members includes an electric element used to apply a treatment energy to the treatment target gripped between the clamp members using an electric energy. A sensor that outputs a detected result to cause a processor to acquire a parameter that varies according to a bent state of the end effector with respect to the tubular sheath and being related to an amount of a gripping force between the clamp members. The electric element is supplied with the electric energy that is output in a state where the processor performs output control at a control target value corresponding to the acquired parameter.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment system comprising:
a power supply device including a processor; and
a treatment tool configured to communicate electrically with the power supply device so as to perform an operation on a treatment target, the treatment tool including:
a sheath, and
an end effector that is detachably attached to the sheath and is capable of bending with respect to the sheath, the end effector including:
a pair of clamp members capable of being opened and closed with respect to one another, and
an electric element configured to receive electric energy and apply a treatment energy to the treatment target using the electric energy,
wherein the processor is configured to:
acquire a parameter that varies according to a bent state of the end effector as a whole with respect to the sheath and is related to an amount of a gripping force between the clamp members, and
set a control target value for controlling the electric energy based on the parameter such that an output of the electric energy to the electric element is higher when the parameter is a first value and a bend angle of the end effector as a whole with respect to the sheath is a first angle that is a largest possible bend angle between the end effector as a whole and the sheath than when the parameter is a second value and the bend angle of the end effector as a whole with respect to the sheath is a second angle that is smaller than the first angle.

2. The treatment system of claim 1, wherein the processor is configured to acquire the parameter based on a detected result from a sensor disposed on the treatment tool.

3. The treatment system of claim 1, wherein the processor is configured to acquire, as the parameter, the bend angle of the end effector as a whole with respect to the sheath.

4. The treatment system of claim 1, further comprising an elongated member for transmitting a drive force to bend the end effector,
wherein the processor is configured to acquire, as the parameter, a displacement of the elongated member when the end effector as a whole bends with respect to the sheath.

5. The treatment system of claim 1, further comprising:
an elongated member for transmitting a drive force to bend the end effector; and
an operating member for moving the elongate member,
wherein the processor is configured to acquire, as the parameter, a displacement or a displaced angle of the operating member when the end effector as a whole bends with respect to the sheath.

6. The treatment system of claim 1, wherein the processor is configured to acquire either a pressure acting on the clamp members or a gap between the clamp members as the parameter.

7. The treatment system of claim 1, wherein the processor is configured to acquire, as the parameter, a change in an angle between the clamp members during closing movement of the clamp members.

8. The treatment system of claim 1, wherein the processor is configured to acquire, as the parameter, an amount of movement or an angle change of a member for transmitting a drive force to open or close the clamp members with respect to one another, as the member operates in ganged relation to closing movement of the clamp members.

9. The treatment system of claim 8, wherein the processor is configured to acquire either an amount of movement of a drive shaft movable to open or close the clamp members with respect to one another, as the drive shaft operates in ganged relation to closing movement of the clamp members, or an angle change of a handle through which an operation input to open or close the clamp members with respect to one another is entered, as the handle operates in ganged relation to closing movement of the clamp members, as the amount of movement or the angle change.

10. The treatment system of claim 1, wherein
when the parameter is the first value, the amount of the gripping force between the clamp members is a first amount of force, and when the parameter is the second value, the amount of the gripping force between the clamp members is a second amount of force larger than the first amount of force.

11. A treatment system comprising:
a power supply device including a processor; and
a treatment tool configured to communicate electrically with the power supply device so as to perform an operation on a treatment target, the treatment tool including:
  a tubular sheath extending from a proximal end to a distal end,
  a housing detachably attached to the proximal end of the tubular sheath, and
  an end effector that is detachably attached to the distal end of the tubular sheath and is capable of bending with respect to the tubular sheath, the end effector including a pair of clamp members capable of being opened and closed with respect to one another, the pair of clamp members including an electric element configured to receive an electric energy and apply a treatment energy to the treatment target gripped between the clamp members using the electric energy,
wherein the processor is configured to:
  acquire a parameter that varies according to a bent state of the end effector as a whole with respect to the tubular sheath and is related to an amount of a gripping force between the clamp members, and
  set a control target value for controlling an output of the electric energy to the electric element based on the acquired parameter such that the output of the electric energy to the electric element is higher when the parameter is a first value and a bend angle of the end effector as a whole with respect to the tubular sheath is a first angle that is a largest possible bend angle between the end effector as a whole and the tubular sheath than when the parameter is a second value and the bend angle of the end effector as a whole with respect to the tubular sheath is a second angle that is smaller than the first angle.

12. The treatment system of claim 11, further comprising a sensor for transmitting a detected result to the processor, wherein the processor is configured to acquire the parameter based on the detected result from the sensor.

13. A treatment tool comprising:
a housing;
a tubular sheath extending from a proximal end to a distal end, the proximal end of the tubular sheath being detachably attached to the housing;
an end effector that is detachably attached to the distal end of the tubular sheath and is capable of bending with respect to the tubular sheath, the end effector including a pair of clamp members capable of being opened and closed with respect to one another, the pair of clamp members including an electric element configured to receive an electric energy and apply a treatment energy to the treatment target gripped between the clamp members using the electric energy; and
a sensor that is configured to output to a processor a detected value of a parameter that varies according to a bent state of the end effector as a whole with respect to the tubular sheath and is related to an amount of a gripping force between the clamp members,
wherein the electric element is configured to be supplied with the electric energy that is output based on a target control value determined by the processor based on the detected value of the parameter such that the output of the electric energy to the electric element is higher when the parameter is a first value and a bend angle of the end effector as a whole with respect to the tubular sheath is a first angle that is a largest possible bend angle between the end effector as a whole and the tubular sheath than when the parameter is a second value and the bend angle of the end effector as a whole with respect to the tubular sheath is a second angle that is smaller than the first angle.

* * * * *